(12) United States Patent
Remillard et al.

(10) Patent No.: US 7,964,573 B2
(45) Date of Patent: Jun. 21, 2011

(54) REGULATING EXPRESSION OF TRANSIENT RECEPTOR POTENTIAL CHANNEL GENES

(75) Inventors: Carmelle Remillard, San Diego, CA (US); Lewis J. Rubin, La Jolla, CA (US); Ying Yu, Lake Forest, CA (US); Jason X.-J. Yuan, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 582 days.

(21) Appl. No.: 11/814,038

(22) PCT Filed: Jan. 17, 2006

(86) PCT No.: PCT/US2006/001993
§ 371 (c)(1),
(2), (4) Date: Oct. 9, 2007

(87) PCT Pub. No.: WO2006/076735
PCT Pub. Date: Jul. 20, 2006

(65) Prior Publication Data
US 2008/0118497 A1    May 22, 2008

Related U.S. Application Data

(60) Provisional application No. 60/643,809, filed on Jan. 14, 2005, provisional application No. 60/643,806, filed on Jan. 15, 2005.

(51) Int. Cl.
*A01N 43/04* (2006.01)
*A61K 31/70* (2006.01)
*A61K 39/00* (2006.01)
*A61K 39/38* (2006.01)
*A61K 38/00* (2006.01)

(52) U.S. Cl. ............................ 514/44; 424/184.1; 514/2
(58) Field of Classification Search ................... 514/44, 514/2; 424/184.1
See application file for complete search history.

(56) References Cited

U.S. PATENT DOCUMENTS
2004/0092475 A1 * 5/2004 Li et al. ........................... 514/44

OTHER PUBLICATIONS

Kunichika et al. (Am. J. Respir. Crit. Care Med. 170, 1101-1107, 2004.*
Yu et al. (AJP Cell Physiol 284: C316-C330, 2003).*
Harborth et al. (2001) J. Cell Science 114:4557-4565.*
Holen et al. (2002) Nucleic Acids Res. 30:1757-1766.*
Boese et al., "Mechanical Insights Aid Computational Short Interfering RNA Design," Methods in Enzymology 392:73-96, 2005.*
Reynolds et al., "Rational siRNA design for RNA interference," Nature Biotechnology 22:326-330, 2004.*
Yu, Ying et al., "Enhanced expression of transient receptor potential channels in idiopathic pulmonary arterial hypertension," Proceedings of the National Academy of Sciences of the United States of America (2004), 101(38), 13861-13866.

* cited by examiner

*Primary Examiner* — Brian Whiteman
(74) *Attorney, Agent, or Firm* — RatnerPrestia

(57) ABSTRACT

The present invention relates to compositions related to a polynucleotide encoding a transient receptor potential channel gene. Also disclosed is the use of this polynucleotide, its homologs, fragments, variants and its resultant polypeptides in the diagnosis, prevention and treatment of disease, particularly idiopathic pulmonary arterial hypertension (IPAH). This invention also teaches the use of these polynucleotides and polypeptides as assays for drug discovery and therapies.

11 Claims, 9 Drawing Sheets

Figure 1:
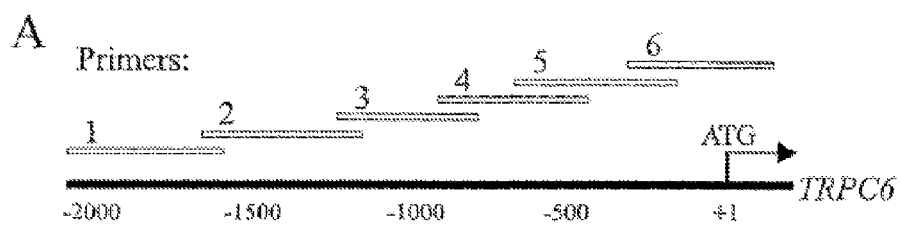
Figure 1:
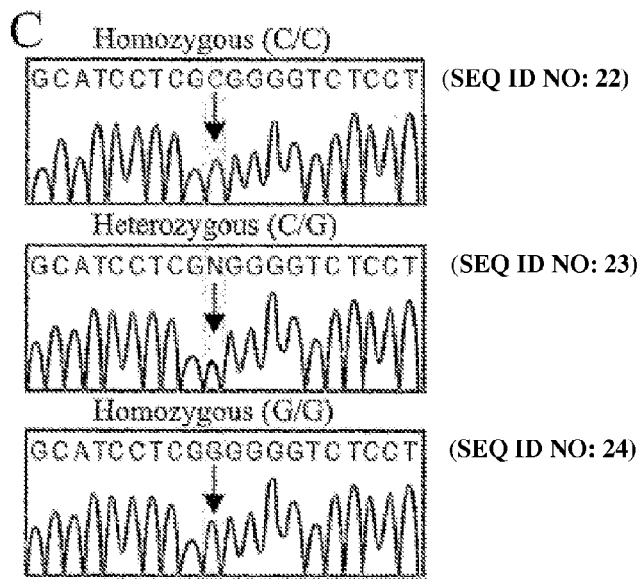

†NF-κB binding site = SEQ ID NO: 26 and SEQ ID NO: 27

```
                              SEQUENCE LISTING

<160> NUMBER OF SEQ ID NOS: 29

<210> SEQ ID NO 1
<211> LENGTH: 11
<212> TYPE: DNA
<213> ORGANISM: Homo sapiens

<400> SEQUENCE: 1
ggggactttc c                                                           11

<210> SEQ ID NO 2
<211> LENGTH: 4564
<212> TYPE: DNA
<213> ORGANISM: Homo sapiens

<400> SEQUENCE: 2
ccgggatctt gacggagagt gcggggatg aaggcgggag ctgagggctg gagagtctct       60
gttgacatag taactcttca gctccgtctc ccttgctctc cgctcttacg cttcgctacc     120
accagcggcc ccgcctgtgc cctctctgcc cgggcgcccc agacgcatcc tcgcggggtc     180
tcctcggcct gacctgctca ggtcaagatc ctctttgcac ccccttaagt ggtgactttt     240
ccccgggcca gtgggcgagc cacttgcggc gggcgtctgc accccctgct tcaccgtcgt     300 ccctgggca ccggtctgcc caggtccagt tcggccgctg acgcgaaccc tccgcaccgg     360
gtccccgctg gaactgccca ctcggctccc ccgggagcgg ggcccaggcc agtcgggcgt     420
tcccgccatg agccagagcc cggcgttcgg gccccggagg ggcagttctc cccggggcgc     480
tgccggagcc gctgcgcggc gcaacgagag ccaggactat ctgctcatgg actcggagct     540
gggagaagac ggctgcccgc aagccccgct gccttgctac ggctactacc cctgcttccg     600
gggatctgac aacagactgg ctcaccgcg gcagacagtt ctccgtgaga aggggagaag     660
gttagctaat cgaggaccag catacatgtt tagtgatcgc tccacaagcc tatctataga     720
ggaggaacgc tttttggatg cagctgaata tggtaacatc ccagtggtgc ggaagatgtt     780
agaagaatgc cactcactca acgttaactg tgtggattac atgggccaga atgccctaca     840
gttggcagtg gccaatgagc atctggaaat tacagaactt cttctcaaga aagaaaacct     900
ctctcgagtt ggggatgctt tgcttctagc tattagtaaa ggttatgttc ggattgtgga     960
agcaattctc agtcatccgg cttttgctga aggcaagagg ttagcaacca gccctagcca    1020
gtctgaactc cagcaagatg atttttatgc ctatgatgaa gatgggacac ggttctccca    1080
tgatgtgact ccaatcattc tggctgccca ctgccaggaa tatgaaattg tgcataccct    1140
cctgcggaag ggtgctagga ttgaacggcc tcatgattat ttctgcaagt gcaatgactg    1200
caaccagaaa cagaagcatg actcgtttag ccactccaga tctaggatta atgcctataa    1260
aggcctggca agtccggctt acctgtcatt gtctagtgaa gatccagtca tgacggcttt    1320
```

```
agaacttagc aatgaactgg cagttctggc caatattgag aaagagttca agaatgacta    1380
caaaaaactg tcaatgcagt gcaaagactt tgttgttgga ctccttgatc tgtgcagaaa    1440
cactgaagaa gtcgaggcca ttctgaatgg ggatgttgaa acgctccaga gtggtgatca    1500
cggtcgccca atctcagcc gtttaaaact tgccattaaa tatgaagtaa aaaaatttgt     1560
agctcatcca aactgccaac agcaacttct ctccatttgg tatgagaatc tttctggttt    1620
acgacagcag acaatggcgg tcaagttcct tgtggtcctt gctgttgcca ttggactgcc    1680
cttcctggct ctcatttact ggtttgctcc atgcagcaag atggggaaga taatgcgtgg    1740
accattcatg aagtttgtag cacacgcagc ctccttcacc atttttctgg gactgctagt    1800
catgaatgca gctgacagat ttgaaggcac aaaactcctt cctaatgaaa ccagcacaga    1860
taatgcaaaa cagctgttca ggatgaaaac atcctgcttc tcatggatgg agatgctcat    1920
tatatcctgg gtaataggca tgatatgggc tgaatgtaaa gaaatctgga ctcagggccc    1980
caaggaatat ttgtttgagt tgtggaacat gcttgatttt ggtatgttag caattttcgc    2040
agcatcattc attgcgagat tcatggcatt ttggcatgct ccaaagccc agagcatcat    2100
tgacgcaaat gatactttga aggacttgac gaaagtaaca ttgggagaca atgtgaaata    2160
ctacaatttg gccaggataa agtgggaccc ctctgatcct caaataatat ctgaaggtct    2220
ttatgcaatt gctgtagttt taagtttctc taggatagct tatatttttac cagcaaatga    2280
aagctttgga cctctgcaga tatcacttgg aagaacagtc aaagacatct tcaagttcat    2340
ggtcatattc attatggtgt ttgtggcctt tatgattgga atgttcaatc tctactccta    2400
ctacattggt gcaaaacaaa atgaagcctt cacaacagtt gaagagagtt ttaagacact    2460
gttctgggct atatttggac tttctgaagt gaaatcagtg gtcatcaact ataaccacaa    2520
attcattgaa acattggtt acgttcttta tggagtctat aatgttacga tggtcattgt    2580
tttgctaaat atgttaattg ccatgatcaa cagttcattc caggaaattg aggatgacgc    2640
tgatgtggag tggaaatttg caagggccaa actctggttt tcctactttg aggagggcag    2700
aacacttcct gtaccttca atctggtgcc gagtccaaag tccctgtttt atctcttact    2760
gaagcttaaa aaatggattt ctgagctgtt ccagggccat aaaaaaggtt ccaggaaga    2820
tgcagagatg aacaagataa atgaagaaaa gaaacttgga attttaggaa gtcatgaaga    2880
cctttcaaaa ttatcacttg acaaaaaaca ggttgggcac aataaacaac caagtataag    2940
gagctcagaa gatttccatc taaatagttt caataatcct ccaagacaat atcagaaaat    3000
aatgaaaagg ctcattaaaa gatatgtact gcaggcccag atagataagg agagtgatga    3060
agtgaacgaa ggggaactga aggaaattaa gcaggacatc tcaagtctcc gctatgaact    3120
ccttgaagaa aaatctcaga atacagaaga cctagcagaa cttattagag aacttggaga    3180
gaaattatcc atggaaccaa atcaagagga aaccaataga taatgcgaag acttccttag    3240
aaattcatat ttatttgtcc acttgaagcc atattatttt ctgatttatt ttcttaagtg    3300
ccaatgggcc caccttttaa acaagaaaac gttaaataac ttgggccatc ctatcatctg    3360
gagccctagt atctaatttt tttggtgatt aaactccatt gttcagggta aaggctgtag    3420
ataatgagga aaattatgcc cagttgtttg gtgcttgttt tataaactgc tttcttggat    3480
ataactaact cttgtgatga tgtcattgcc atgtagtgtc tgcctgaaaa tgggtcccag    3540
cggacagggg ctgacccacg ttactcccca tgcggttttt cctctgaagt ttatttcagg    3600
ttccttcttg cctgctctgt ggatcccctg ctggggactc ccagctctga aatttgggaa    3660
aaagtagccc atgggccttt agaatgcttt aatcctttct ttagaatgct gtttaaacac    3720
```

-continued

```
catttaccct acttatccct caatgcacat gattgatacc gttcatacaa aatggtctta    3780
catctatgta aaattttctg attcatctat ttgaaaacat tacacttaac aatgaaaaaa    3840 gttttttcctc cactgaaccc tggaaacatg gtccagtttt tgtgtgtgtgc gtgtgtgtaa    3900
atgtgtacac acagacataa agtacttgcc ctatttagtt tgtggctaat gtggacacac    3960
aaaagctctt tatgttataa attttttattg tcactaaaaa attttactgt ctaaataagt    4020 acctttttatt ggagaaaaat caaaacccca aacaaacact gtggttgttt ggttccatta    4080
tagcacaatt ttgtgccatt tctgggagca tttacagatg aatccccaca cttagccatt    4140
gaatgtaaag gggaaaaata aggtgagaat ttgtaaatac ttatctgtta ttttcaatat    4200
gttctatcct tctacccaaa tatataaaac aggaatttgc attcatgtgc atttaccaag    4260
aggttgttgt tgttacttac tgatcatgtg aagtggtgtc ttaaacaact aaaagcgatg    4320
aaggttcata tgtttactca aagaccattg gcattcagag gatgctggac attaactgga    4380
actgctactt ccaattcaat aatgggagat ttcaaatgca aatctttaac ttcatcttaa    4440
agatgaaatg gttgcagaaa atctgtttag ctccaacttt ggcttaattt aaatcaaaga    4500
acatttatgt aaccagatca gaaaatacag ctgaaaattt ggaattcgag ctcggtaccc    4560
gggg                                                                  4564
```

<210> SEQ ID NO 3
<211> LENGTH: 931
<212> TYPE: PRT
<213> ORGANISM: Homo sapiens

<400> SEQUENCE: 3

```
Met Ser Gln Ser Pro Ala Phe Gly Pro Arg Arg Gly Ser Ser Pro Arg
1               5                   10                  15

Gly Ala Ala Gly Ala Ala Ala Arg Arg Asn Glu Ser Gln Asp Tyr Leu
            20                  25                  30

Leu Met Asp Ser Glu Leu Gly Glu Asp Gly Cys Pro Gln Ala Pro Leu
        35                  40                  45

Pro Cys Tyr Gly Tyr Tyr Pro Cys Phe Arg Gly Ser Asp Asn Arg Leu
    50                  55                  60

Ala His Arg Arg Gln Thr Val Leu Arg Glu Lys Gly Arg Arg Leu Ala
65                  70                  75                  80

Asn Arg Gly Pro Ala Tyr Met Phe Ser Asp Arg Ser Thr Ser Leu Ser
                85                  90                  95

Ile Glu Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
        115                 120                 125

Val Asp Tyr Met Gly Gln Asn Ala Leu Gln Leu Ala Val Ala Asn Glu
    130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
        195                 200                 205

Tyr Asp Glu Asp Gly Thr Arg Phe Ser His Asp Val Thr Pro Ile Ile
    210                 215                 220
```

```
Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
            245                 250                 255

Asp Cys Asn Gln Lys Gln Lys His Asp Ser Phe Ser His Ser Arg Ser
                260                 265                 270

Arg Ile Asn Ala Tyr Lys Gly Leu Ala Ser Pro Ala Tyr Leu Ser Leu
            275                 280                 285

Ser Ser Glu Asp Pro Val Met Thr Ala Leu Glu Leu Ser Asn Glu Leu
        290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Cys
                325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
        355                 360                 365

Ala Ile Lys Tyr Glu Val Lys Lys Phe Val Ala His Pro Asn Cys Gln
370                 375                 380

Gln Gln Leu Leu Ser Ile Trp Tyr Glu Asn Leu Ser Gly Leu Arg Gln
385                 390                 395                 400

Gln Thr Met Ala Val Lys Phe Leu Val Val Leu Ala Val Ala Ile Gly
                405                 410                 415

Leu Pro Phe Leu Ala Leu Ile Tyr Trp Phe Ala Pro Cys Ser Lys Met
            420                 425                 430

Gly Lys Ile Met Arg Gly Pro Phe Met Lys Phe Val Ala His Ala Ala
        435                 440                 445

Ser Phe Thr Ile Phe Leu Gly Leu Leu Val Met Asn Ala Ala Asp Arg
450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
                485                 490                 495

Leu Ile Ile Ser Trp Val Ile Gly Met Ile Trp Ala Glu Cys Lys Glu
            500                 505                 510

Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
                565                 570                 575

Lys Tyr Tyr Asn Leu Ala Arg Ile Lys Trp Asp Pro Ser Asp Pro Gln
            580                 585                 590

Ile Ile Ser Glu Gly Leu Tyr Ala Ile Ala Val Val Leu Ser Phe Ser
        595                 600                 605

Arg Ile Ala Tyr Ile Leu Pro Ala Asn Glu Ser Phe Gly Pro Leu Gln
610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
```

```
                    645                 650                 655
Ser Tyr Tyr Ile Gly Ala Lys Gln Asn Glu Ala Phe Thr Thr Val Glu
            660                 665                 670

Glu Ser Phe Lys Thr Leu Phe Trp Ala Ile Phe Gly Leu Ser Glu Val
        675                 680                 685

Lys Ser Val Val Ile Asn Tyr Asn His Lys Phe Ile Glu Asn Ile Gly
    690                 695                 700

Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
                725                 730                 735

Asp Ala Asp Val Glu Trp Lys Phe Ala Arg Ala Lys Leu Trp Phe Ser
            740                 745                 750

Tyr Phe Glu Glu Gly Arg Thr Leu Pro Val Pro Phe Asn Leu Val Pro
        755                 760                 765

Ser Pro Lys Ser Leu Phe Tyr Leu Leu Leu Lys Leu Lys Lys Trp Ile
    770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
            820                 825                 830

Lys Gln Pro Ser Ile Arg Ser Ser Glu Asp Phe His Leu Asn Ser Phe
        835                 840                 845

Asn Asn Pro Pro Arg Gln Tyr Gln Lys Ile Met Lys Arg Leu Ile Lys
    850                 855                 860

Arg Tyr Val Leu Gln Ala Gln Ile Asp Lys Glu Ser Asp Glu Val Asn
865                 870                 875                 880

Glu Gly Glu Leu Lys Gly Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Glu Lys Leu Ser Met Glu Pro Asn Gln Glu Glu
        915                 920                 925

Thr Asn Arg
    930

<210> SEQ ID NO 4
<211> LENGTH: 10
<212> TYPE: DNA
<213> ORGANISM: Artificial
<220> FEATURE:
<223> OTHER INFORMATION: Derived from human sequence
<220> FEATURE:
<221> NAME/KEY: misc_feature
<222> LOCATION: (1)..(1)
<223> OTHER INFORMATION: C-G single nucleotide polymorphism in first
      nucleotide

<400> SEQUENCE: 4
gggggtctcc                                                              10

<210> SEQ ID NO 5
<211> LENGTH: 21
<212> TYPE: DNA
<213> ORGANISM: Artificial
<220> FEATURE:
<223> OTHER INFORMATION: Derived from human sequence
```

```
<400> SEQUENCE: 5
aaggtcttta tgcaattgct g                                              21

<210> SEQ ID NO 6
<211> LENGTH: 10
<212> TYPE: DNA
<213> ORGANISM: Artificial
<220> FEATURE:
<223> OTHER INFORMATION: Derived from human sequence
<220> FEATURE:
<221> NAME/KEY: misc_feature
<222> LOCATION: (4)..(4)
<223> OTHER INFORMATION: a or g
<220> FEATURE:
<221> NAME/KEY: misc_feature
<222> LOCATION: (5)..(5)
<223> OTHER INFORMATION: a, c, g or t
<220> FEATURE:
<221> NAME/KEY: misc_feature
<222> LOCATION: (6)..(9)
<223> OTHER INFORMATION: c or t

<400> SEQUENCE: 6 gggrnyyycc                                                           10

<210> SEQ ID NO 7
<211> LENGTH: 21
<212> TYPE: DNA
<213> ORGANISM: Artificial
<220> FEATURE:
<223> OTHER INFORMATION: Derived from human sequence

<400> SEQUENCE: 7
ttccccatac ttggtgttgc c                                              21

<210> SEQ ID NO 8
<211> LENGTH: 20
<212> TYPE: DNA
<213> ORGANISM: Artificial
<220> FEATURE:
<223> OTHER INFORMATION: Derived from human sequence

<400> SEQUENCE: 8
agcagaaacc acttgtcctg                                                20

<210> SEQ ID NO 9
<211> LENGTH: 22
<212> TYPE: DNA
<213> ORGANISM: Artificial
<220> FEATURE:
<223> OTHER INFORMATION: Derived from human sequence

<400> SEQUENCE: 9
cctgtgtcaa atacgaagct gg                                             22

<210> SEQ ID NO 10
<211> LENGTH: 21
<212> TYPE: DNA
<213> ORGANISM: Artificial
<220> FEATURE:
<223> OTHER INFORMATION: Derived from human sequence

<400> SEQUENCE: 10
ggaggcaaag aagcagatga g                                              21

<210> SEQ ID NO 11
<211> LENGTH: 22
```

```
<212> TYPE: DNA
<213> ORGANISM: Artificial
<220> FEATURE:
<223> OTHER INFORMATION: Derived from human sequence

<400> SEQUENCE: 11
aattggtccc cctttctgcc ac                                               22

<210> SEQ ID NO 12
<211> LENGTH: 22
<212> TYPE: DNA
<213> ORGANISM: Artificial
<220> FEATURE:
<223> OTHER INFORMATION: Derived from human sequence

<400> SEQUENCE: 12
aacgccagat gttcccagtt cc                                               22

<210> SEQ ID NO 13
<211> LENGTH: 22
<212> TYPE: DNA
<213> ORGANISM: Artificial
<220> FEATURE:
<223> OTHER INFORMATION: Derived from human sequence

<400> SEQUENCE: 13
ttgcattcgc agtgacggaa gg                                               22

<210> SEQ ID NO 14
<211> LENGTH: 22
<212> TYPE: DNA
<213> ORGANISM: Artificial
<220> FEATURE:
<223> OTHER INFORMATION: Derived from human sequence

<400> SEQUENCE: 14
agaaagcagc caaagcctgt cc                                               22

<210> SEQ ID NO 15
<211> LENGTH: 21
<212> TYPE: DNA
<213> ORGANISM: Artificial
<220> FEATURE:
<223> OTHER INFORMATION: Derived from human sequence

<400> SEQUENCE: 15
agaaagaaga ggctcgtgtc c                                                21

<210> SEQ ID NO 16
<211> LENGTH: 22
<212> TYPE: DNA
<213> ORGANISM: Artificial
<220> FEATURE:
<223> OTHER INFORMATION: Derived from human sequence

<400> SEQUENCE: 16
gaaaagtcac cacttaaggg gg                                               22

<210> SEQ ID NO 17
<211> LENGTH: 22
<212> TYPE: DNA
<213> ORGANISM: Artificial
<220> FEATURE:
<223> OTHER INFORMATION: Derived from human sequence

<400> SEQUENCE: 17
ttgctctccg ctcttacgct tc                                               22
```

```
<210> SEQ ID NO 18
<211> LENGTH: 22
<212> TYPE: DNA
<213> ORGANISM: Artificial
<220> FEATURE:
<223> OTHER INFORMATION: Derived from human sequence

<400> SEQUENCE: 18
tccatgagca gatagtcctg gc                                              22

<210> SEQ ID NO 19
<211> LENGTH: 500
<212> TYPE: DNA
<213> ORGANISM: Homo sapiens

<400> SEQUENCE: 19
gggatcttga cggagagtgc gggggatgaa ggcgggagct gagggctgga gagtctctgt     60
tgacatagta actcttcagc tccgtctccc ttgctctccg ctcttacgct tcgctaccac    120
cagcggcccc gcctgtgccc tctctgcccg ggcgccccag acgcatcctc gcggggtctc    180
ctcggcctga cctgctcagg tcaagatcct ctttgcaccc ccttaagtgg tgacttttcc    240
ccgggccagt gggcgagcca cttgcggcgg gcgtctgcac cccctgcttc accgtcgtcc    300
cctgggcacc ggtctgccca ggtccagttc ggccgctgac gcgaaccctc gcaccgggt    360 ccccgctgga actgcccact cggctccccc gggagcgggg cccaggccag tcgggcgttc    420
ccgccatgag ccagagcccg gcgttcgggc cccggagggg cagttctccc cggggcgctg    480
ccggagccgc tgcgcggcgc                                                500

<210> SEQ ID NO 20
<211> LENGTH: 16
<212> TYPE: PRT
<213> ORGANISM: Homo sapiens

<400> SEQUENCE: 20

Met Ser Gln Ser Pro Ala Phe Gly Pro Arg Arg Gly Ser Ser Pro Arg
1               5                   10                  15

<210> SEQ ID NO 21
<211> LENGTH: 10
<212> TYPE: DNA
<213> ORGANISM: Homo sapiens

<400> SEQUENCE: 21
cggggtctcc                                                            10

<210> SEQ ID NO 22
<211> LENGTH: 20
<212> TYPE: DNA
<213> ORGANISM: Homo sapiens

<400> SEQUENCE: 22
gcatcctcgc ggggtctcct                                                 20

<210> SEQ ID NO 23
<211> LENGTH: 20
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
```

```
<400> SEQUENCE: 23
gcatcctcgn ggggtctcct                                              20

<210> SEQ ID NO 24
<211> LENGTH: 20
<212> TYPE: DNA
<213> ORGANISM: Homo sapiens

<400> SEQUENCE: 24
gcatcctcgg ggggtctcct                                              20

<210> SEQ ID NO 25
<211> LENGTH: 12
<212> TYPE: DNA
<213> ORGANISM: Homo sapiens

<400> SEQUENCE: 25
cgcggggtct cc                                                      12

<210> SEQ ID NO 26
<211> LENGTH: 12
<212> TYPE: DNA
<213> ORGANISM: Homo sapiens

<400> SEQUENCE: 26
cggggggtct cc                                                      12

<210> SEQ ID NO 27
<211> LENGTH: 11
<212> TYPE: DNA
<213> ORGANISM: Homo sapiens

<400> SEQUENCE: 27
aagatcctct t                                                       11

<210> SEQ ID NO 28
<211> LENGTH: 21
<212> TYPE: DNA
<213> ORGANISM: Homo sapiens

<400> SEQUENCE: 28
gacatagtac gcggggtctc c                                            21

<210> SEQ ID NO 29
<211> LENGTH: 21
<212> TYPE: DNA
<213> ORGANISM: Homo sapiens

<400> SEQUENCE: 29
gacttagtac gcggggtctc c                                            21
```

REGULATING EXPRESSION OF TRANSIENT RECEPTOR POTENTIAL CHANNEL GENES

CROSS-REFERENCE TO RELATED APPLICATIONS

This application is a U.S. National of PCT/US2006/001993 filed Jan. 17, 2006 which claims priority from U.S. Provisional Application Ser. No. 60/643,809 filed on Jan. 14, 2005, and U.S. Provisional Application Ser. No. 60/643,806 filed on Jan. 15, 2005, each of which is incorporated herein by reference in its entirety.

STATEMENT REGARDING FEDERALLY SPONSORED RESEARCH OR DEVELOPMENT

This invention was made with Government support under HL-54043, HL-66941, HL-69758, HL-66012 and HL-64945 from the National Heart Lung and Blood Institute (NHLBI; NIH). The Government has certain rights in the invention.

INCORPORATION-BY-REFERENCE OF MATERIAL SUBMITTED ON A COMPACT DISC

The Sequence Listing, which is a part of the present disclosure, includes a computer readable form and a written sequence listing comprising nucleotide and amino acid sequences of the present invention. The sequence listing information recorded in computer readable form is identical to the written sequence listing. The subject matter of the Sequence Listing is incorporated herein by reference in its entirety.

FIELD

The present invention relates to compositions that regulate the expression of the genes encoding mammalian transient receptor potential channel (TRPC) proteins and methods of using the compositions for prevention, diagnosis, and treatment of idiopathic pulmonary arterial hypertension (IPAH).

INTRODUCTION

IPAH is a fatal and progressive disease with unknown etiology and which predominantly affects women. The elevated pulmonary vascular resistance (PVR) and arterial pressure in IPAH patients result mainly from pulmonary vasoconstriction, vascular remodeling, and in situ thrombosis. A central aspect of pulmonary vascular remodeling is medial hypertrophy caused by sustained pulmonary vasoconstriction, excessive pulmonary artery smooth muscle cell (PASMC) proliferation, and inhibited PASMC apoptosis, resulting in a narrowed vascular lumen and increased PVR. Although its etiology remains unclear, elevated levels of circulating mitogens, dysfunction or down-regulation of receptors and ion channels, upregulation of transporters, and heightened activity of elastases and glycoproteins have been implicated in IPAH.

Mutations of certain genes such as bone morphogenic protein (BMP) receptor type II gene (BMPR2) and serotonin transporter gene (5-HTT) have recently been demonstrated to be the genetic basis for familial and idiopathic pulmonary arterial hypertension. BMPs are members of the transforming growth factor-β (TGF-β) superfamily of growth-regulatory proteins. BMPs and TGF-β have recently been considered to influence airway inflammatory processes in adults due to their chemotactic activity on fibroblasts, myocytes, and inflammatory cells. Induction of such inflammatory pathways in, for example, intestinal epithelium and antigen-presenting cells, as well as production of interferons, cytokines, and TNF-α, is known to be mediated by the nuclear factor κB (NF-κB) family of transcription factors.

NF-κB was originally described as a DNA-binding activity that recognized a sequence GGGGACTTTCC (SEQ ID NO: 1) in the immunoglobulin κ light chain gene enhancer in mature B cells. At least five members of heterodimeric mammalian NF-κB have been described: NF-κB1 (p50 and its precursor p105), NF-κB2 (p52 and its precursor p100), c-Rel, RelA (p65) and RelB, each of which has a 300-residue Rel homology domain. The C-terminal domains are responsible for dimerization with other Rel proteins, but sequence-specific interactions come primarily from loops in the N-terminal domain. Members of the NF-κB family have been identified in various organisms, ranging from flies to mammals. Members of this transcription factor family have about 35% to 60% identity to each other and all have the Rel homology domain.

In mammals, the most widely distributed κB-binding transcription factor is a heterodimer consisting of p50 and p65 (Rel-A) proteins. In particular, it controls the expression of various inflammatory cytokines, the major histocompatibility complex genes and adhesion molecules involved in tumor metastasis.

SUMMARY

The present teachings include a method for predicting a mammalian subject's susceptibility to IPAH. This method comprises providing a sample from the subject, wherein the sample comprises a polynucleotide, the polynucleotide corresponding to a TRPC6 gene, providing a treatment process, treating the sample with the treatment process under conditions such that a genotype for IPAH is detected if present, wherein the genotype comprises a genotype homozygous for at least one allele of the polymorphic site at position −254 in SEQ ID NO: 2, and detecting the IPAH genotype if present, wherein the presence of the genotype is indicative of the subject's susceptibility to IPAH. In certain aspects, the mammalian subject is a human subject. In other aspects, the sample is lung tissue. In certain aspects, the sample is blood.

In yet another aspect, a method is provided for screening for IPAH in a mammalian subject, the method comprising obtaining a sample from the subject, contacting the sample with a polynucleotide specific to a single nucleotide polymorphism corresponding to position −254 of SEQ ID NO: 2, and detecting whether the polynucleotide hybridizes with the sample.

In a further aspect, a method is provided for treating IPAH, the method comprising administering to a subject in need thereof a therapeutically effective amount of a compound that reduces the level of mRNA encoding TRPC6 polypeptide, a compound that reduces the level of TRPC6 polypeptide, or a compound that reduces a biological activity of TRPC6. In certain embodiments, the subject is a mammal. In certain embodiments, the mammal is a human. In yet another aspect, the compound is selected from the group consisting of an siRNA, antisense nucleic acid, a ribozyme, an antibody, a polypeptide fragment, and a peptidomimetic.

In yet another aspect, a method is provided for detecting a susceptibility to or presence IPAH in a subject comprising obtaining a biological sample of the subject, and contacting the biological sample with SNP-specific antibody, wherein the binding of the antibody biological sample is indicative of a susceptibility to or presence of IPAH in the subject. In certain aspects, the antibody is a monoclonal antibody. In certain aspects, the antibody is specific to a variant of TRPC6. In certain aspects, the antibody is specific to a fragment of TRPC6.

In another aspect, an inhibitor of TRPC6 is provided, wherein said inhibitor is selected from the group consisting of a compound that reduces the level of mRNA encoding TRPC6 polypeptide, a molecule that reduces the level of TRPC6 polypeptide, and a molecule that reduces a biological activity of TRPC6. In certain aspects, the inhibitor is selected from the group consisting of an siRNA, antisense nucleic acid, a ribozyme, an antibody, a peptide, and a peptidomimic. In certain aspects, the inhibitor is a SNP-specific antibody. In certain aspects, the siRNA comprises a polynucletide having SEQ ID NO:5.

In yet another aspect, an isolated polynucleotide having NF-κB activity is provided, wherein said polynucleotide comprises SEQ ID NO: 2. In still a further aspect, an isolated and purified polynucleotide is provided comprising SEQ ID NO: 2. In yet another aspect, an expression vector is provided, wherein said vector comprises a polynucleotide encoding a siRNA molecule targeted against a portion of a TRPC6 gene. In certain aspects, the portion of the TRPC6 gene comprises a single nucleotide polymorphism corresponding to position −254 of SEQ ID NO: 2.

In yet another aspect, a kit is provided for screening for a therapeutic agent to treat IPAH wherein the kit comprises: (i) a polynucleotide comprising the nucleotide sequence of an oligonucleotide having at least 10 nucleotides and comprising a nucleotide sequence that is complementary to the complementary strand of the polynucleotide, and (ii) a cell expressing the marker gene, wherein the marker gene corresponds to SEQ ID NO: 2.

In further aspect, a monoclonal antibody as described above is provided. In another aspect, an antibody specific to a variant of TRPC6 as described above is provided. In another aspect, an antibody specific to a fragment of TRPC6 as described above is provided.

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 1. Diagram showing positions of the primers used to amplify the human TRPC6 gene promoter (FIG. 1A); the sequence of each primer is listed in Table 12. Sequence of the wild-type TRPC6 promoter region (FIG. 1B) with the SNP and flanking sequences underlined. The portion of the TRPC6 gene illustrated (SEQ ID NO: 19) represents nucleotides 3 through 502 of SEQ ID NO: 2 and the portion of the TRPC6 polypeptide illustrated (SEQ ID NO: 20) represents amino acids 1 through 16 of SEQ ID NO: 3. The C-254G SNP changed the wild-type sequence CGGGGTCTCC (SEQ ID NO: 21; depicted in box) of SEQ ID NO: 2 to GGGGGTCTCC (SEQ ID NO: 4); which becomes a potential NF-κB binding site, GGGRNYYYCC (SEQ ID NO: 6) described more fully below. The −254 SNP corresponds to nucleotide 174 of SEQ ID NO: 2. Examples of chromatograms showing the homozygous CC (GCATCCTCGCGGGTCTCCT, SEQ ID NO: 22), heterozygous CG (GCATCCTCGNGGGTCTCCT, SEQ ID NO: 23), or homozygous GG (GCATCCTCGGGGGGTCTCCT, SEQ ID NO: 24) genotype (FIG. 1C; sequenced from three IPAH patients). Alignment of the sequences including the −254 SNP (CGCGGGGTCTCC SEQ ID NO: 25 and CGGGGGGTCTCC, SEQ ID NO: 26) illustrating C-254G and the sequences including the −361 SNP (GACATAGTA and GACTTAGTA) illustrating A-361T SNPs from 17 IPAH patients (FIG. 1D).

Figure 2:
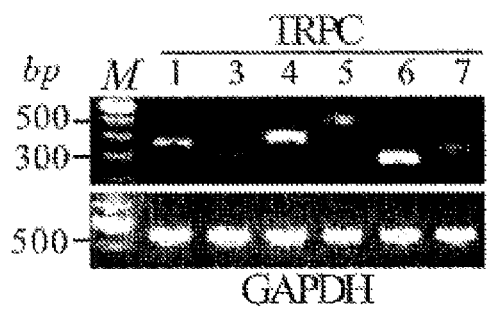
Figure 2:
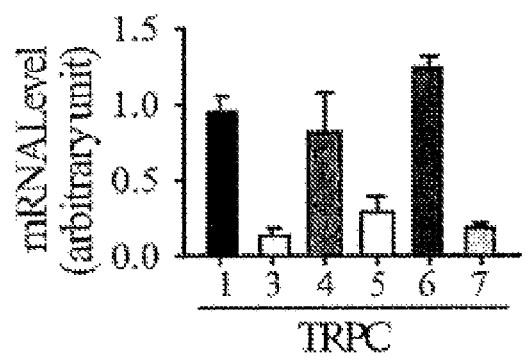
Figure 2:
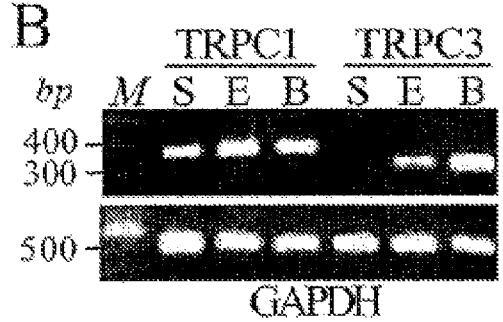
Figure 2:
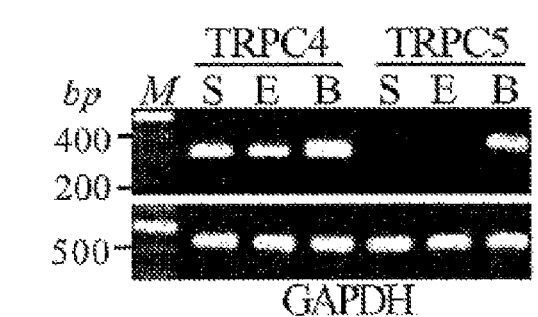
Figure 2:
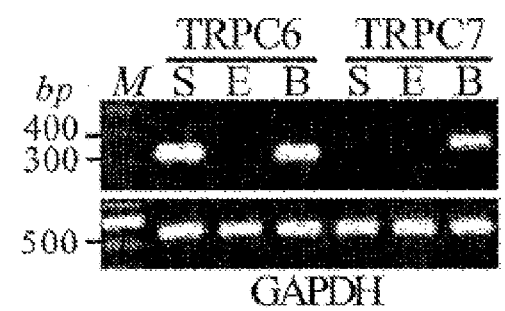
Figure 2:
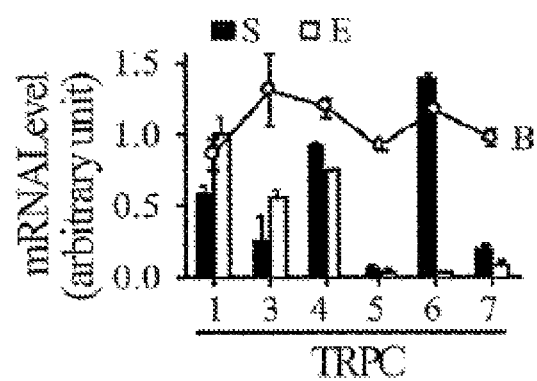

FIG. 2. The mRNA expression of TRPC channels in NPH lung tissue and PASMC. (A) Representative and summarized (n=4) mRNA products for TRPC genes and GAPDH in NPH human lung. (B) Representative and summarized (n=3) data showing TRPC gene mRNA products in human brain tissue (B), PASMC (S), and PAEC (E). M=100 bp DNA ladder.

Figure 3:
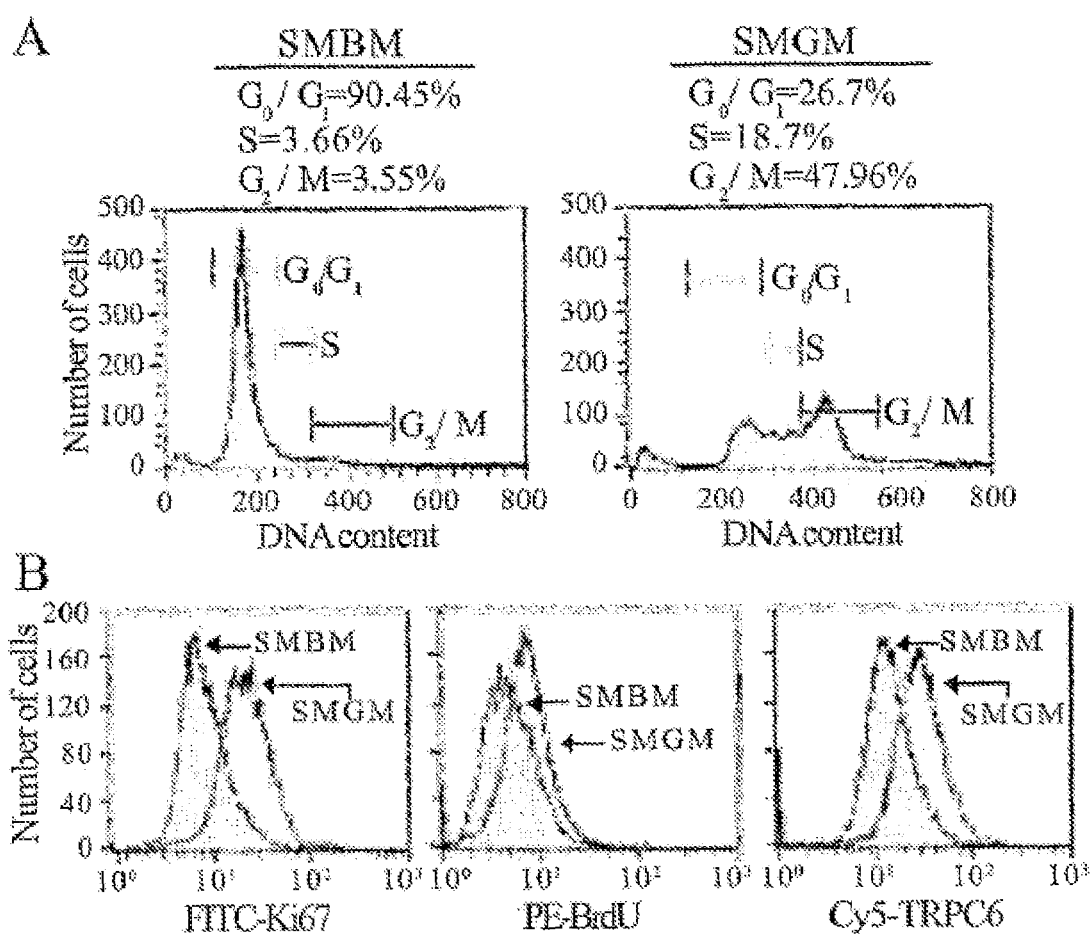

FIG. 3. Cell cycle analysis of growth-arrested and proliferating PASMC and correlation of TRPC6 expression with PASMC proliferation. (A) Flow cytometry histograms (representative of 3 trials) of cell cycle analysis for growth-arrested (SMBM) and proliferating (SMGM) PASMC. Number of cells is plotted as a function of DNA content. (B) Histograms showing cell number as a function of Ki67 expression, BrdU incorporation, or TRPC6 expression in SMBM- and SMGM-treated PASMC.

Figure 4:
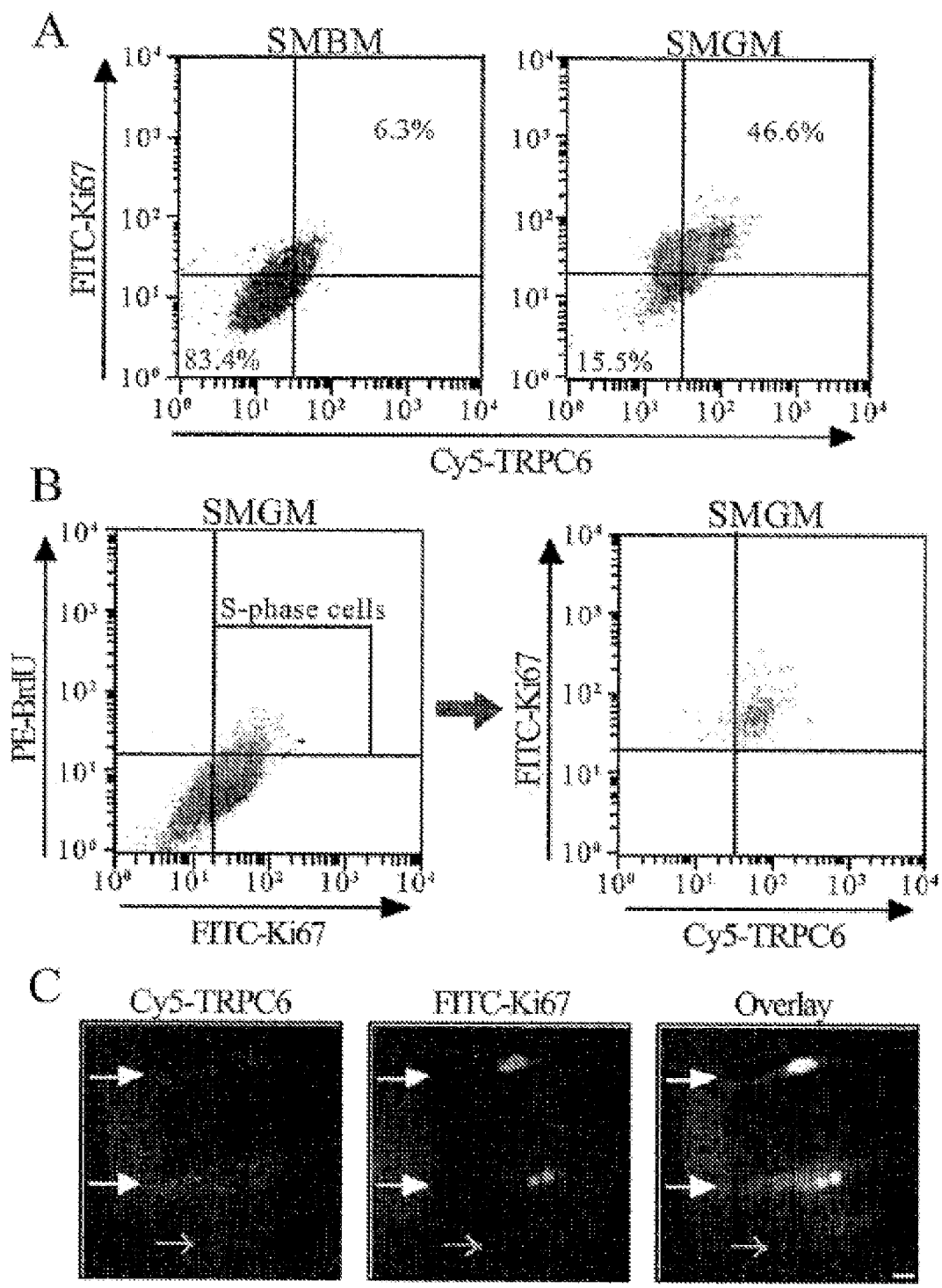

FIG. 4. Correlation of Ki67 expression and BrdU incorporation with TRPC6 expression. (A) Dot-plot analysis (representative of 3 trials) of TRPC6 expression versus Ki67 expression in growth-arrested and proliferating PASMC. Upper right quadrants represent cells in the S phase. (B) Three-color dot-plot analysis of TRPC6 distribution versus BrdU incorporation and Ki67 expression in proliferating PASMC (representative of 3 trials). The box in the left panel indicates the S-phase cells that are stained by both Ki67 and BrdU. (C) Fluorescent images (×40) showing PASMC stained by Ki67 and TRPC6. An overlay of the two fluorescent images identifies PASMC expressing both Ki67 and TRPC6. Yellow arrows (top two bold arrows per panel) and green arrows (bottom arrow per panel) indicate Ki67-positive and -negative PASMC, respectively. (Scale bar, 20 μm.)

Figure 5:
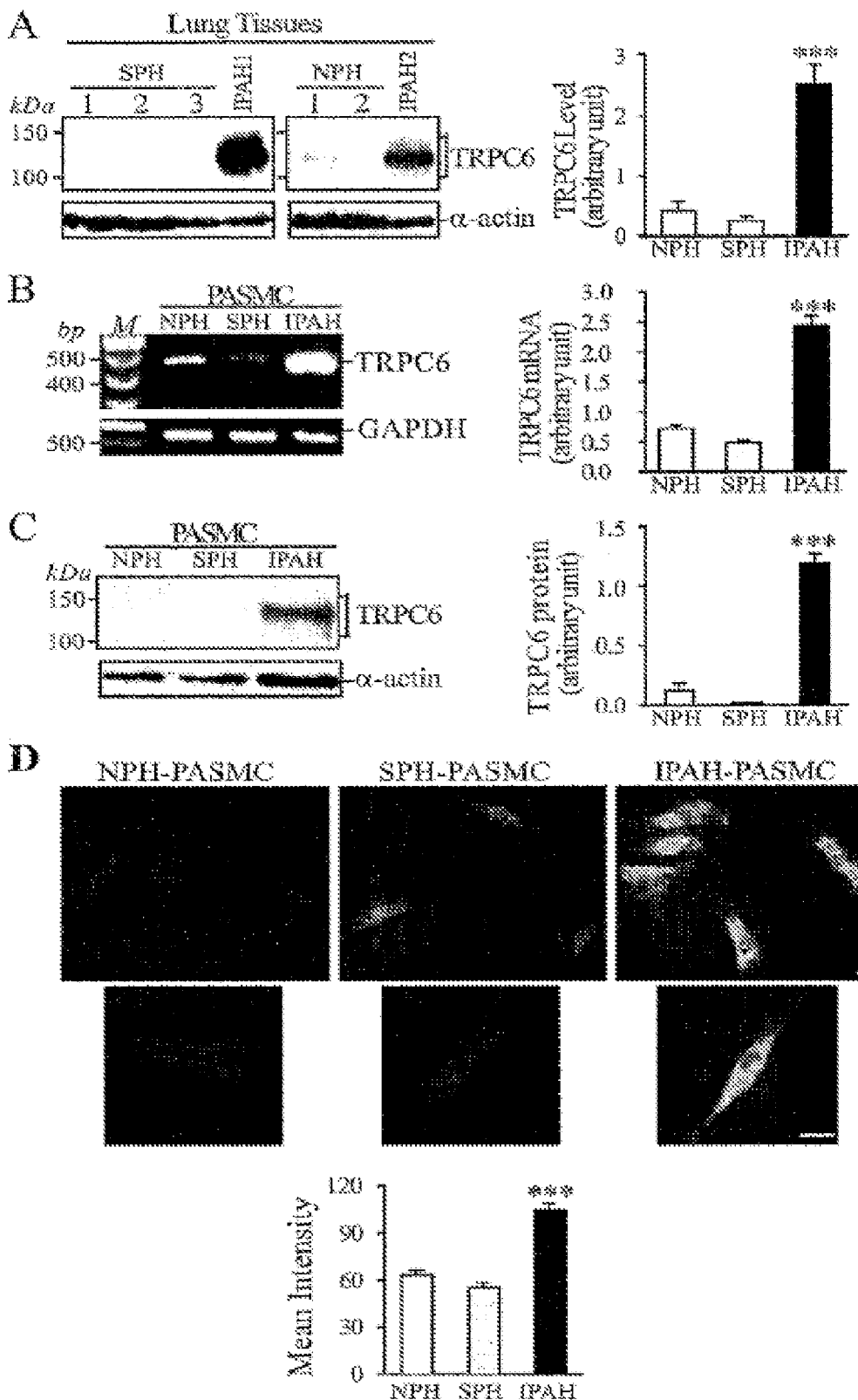

FIG. 5. TRPC6 mRNA and protein expression is increased in pulmonary tissues from IPAH patients. (A) Representative and summarized (NPH, n=3; SPH, n=8; IPAH, n=3; normalized to α-actin) TRPC6 protein expression in SPH, NPH, and IPAH lung tissues and their α-actin controls. (B) Representative and summarized (n=3 for each) data showing TRPC6 mRNA products in isolated NPH-, SPH, or IPAH-PASMC. M, 100 bp DNA ladder. (C) Representative and summarized (n=5 for each) TRPC6 protein expression in isolated PASMC from NPH, SPH, and IPAH patients. (D) Representative (×40, upper panels and ×100, middle panels) and summarized immunofluorescence staining of FITC-conjugated TRPC6 (lower panel) in isolated NPH- (n=11), SPH (n=21), and IPAH- (n=36) PASMC. (Scale bars, 20 μm.) (***, P<0.001 vs. NPH and/or SPH.)

Figure 6:
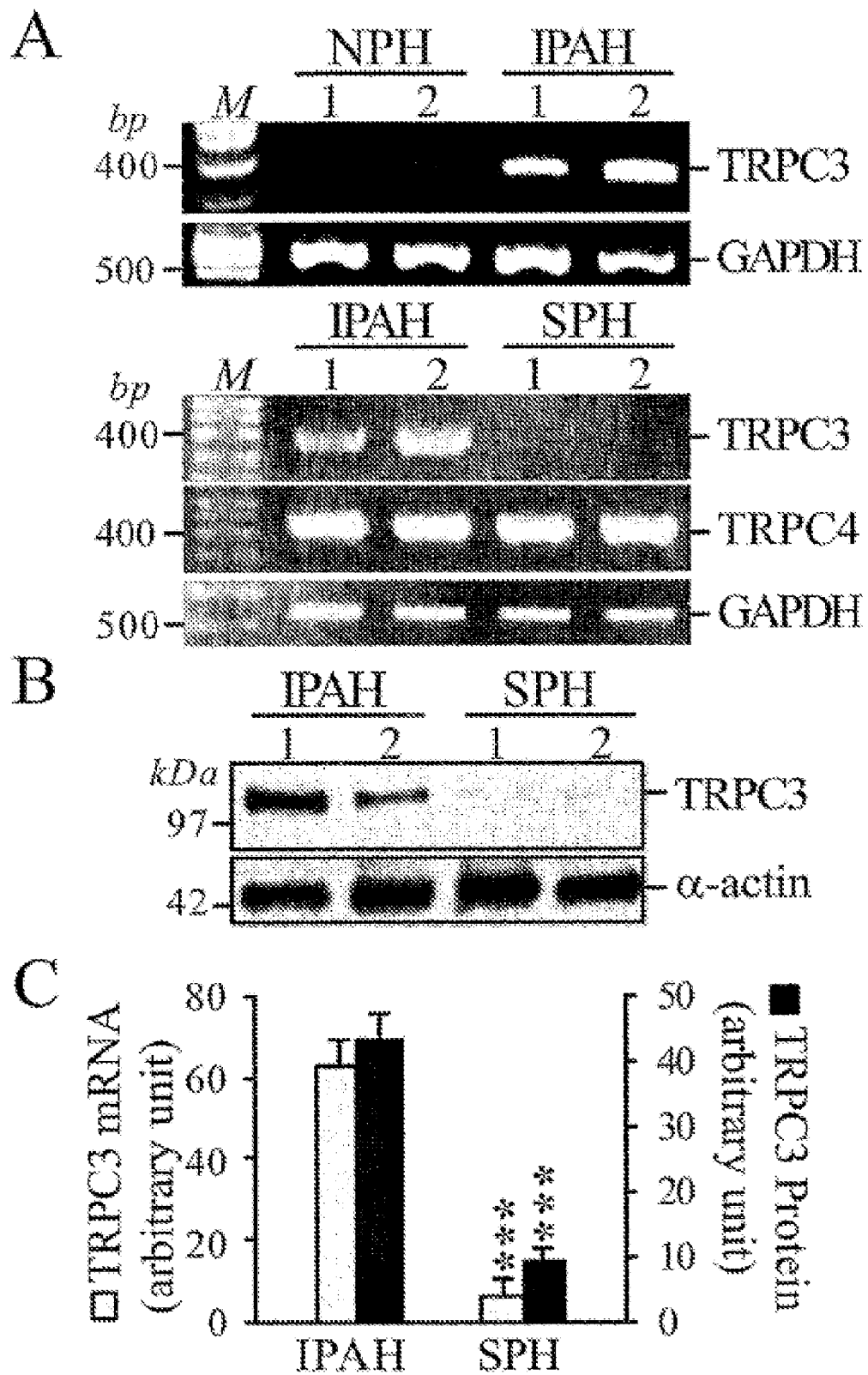

FIG. 6. Upregulated TRPC3 expression in IPAH-PASMC. (A) TRPC3 mRNA expression in PASMC from two NPH patients and two IPAH patients. TRPC3 and 4 mRNA expression in PASMC from two IPAH patients and two SPH patients. M, 100 bp DNA ladder. (B) TRPC3 protein expression in the same IPAH and SPH samples as shown in A. (C) Summarized bar graphs (n=3 for each) depicting normalized TRPC3 mRNA and protein expression. (***, P<0.001 vs. IPAH.)

Figure 7:
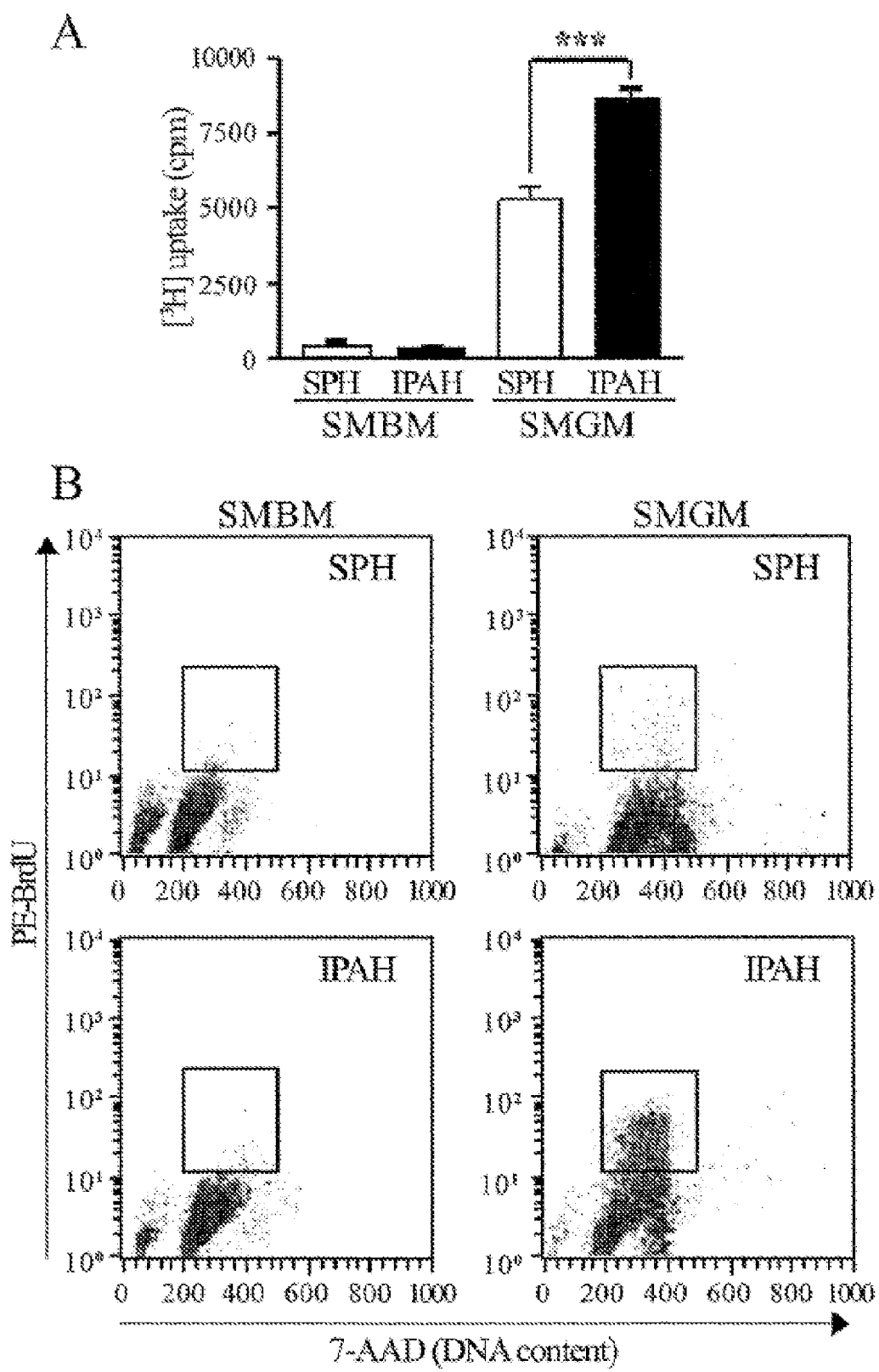

FIG. 7. Increased proliferation of IPAH-PASMC. (A) [$^3$H]-Thymidine incorporation in SPH- (n=8) and IPAH- (n=8) PASMC before (12 h SMBM) and 24 h after the addition of 5% FBS and growth factors (SMGM). (***, P<0.001 versus SMGM-SPH.) (B) Bivariate distribution of BrdU versus DNA content for SMBM- or SMGM-treated SPH- and IPAH-PASMC. Boxes indicate S phase PASMC. Data are representative of 3 experiments.

Figure 8:
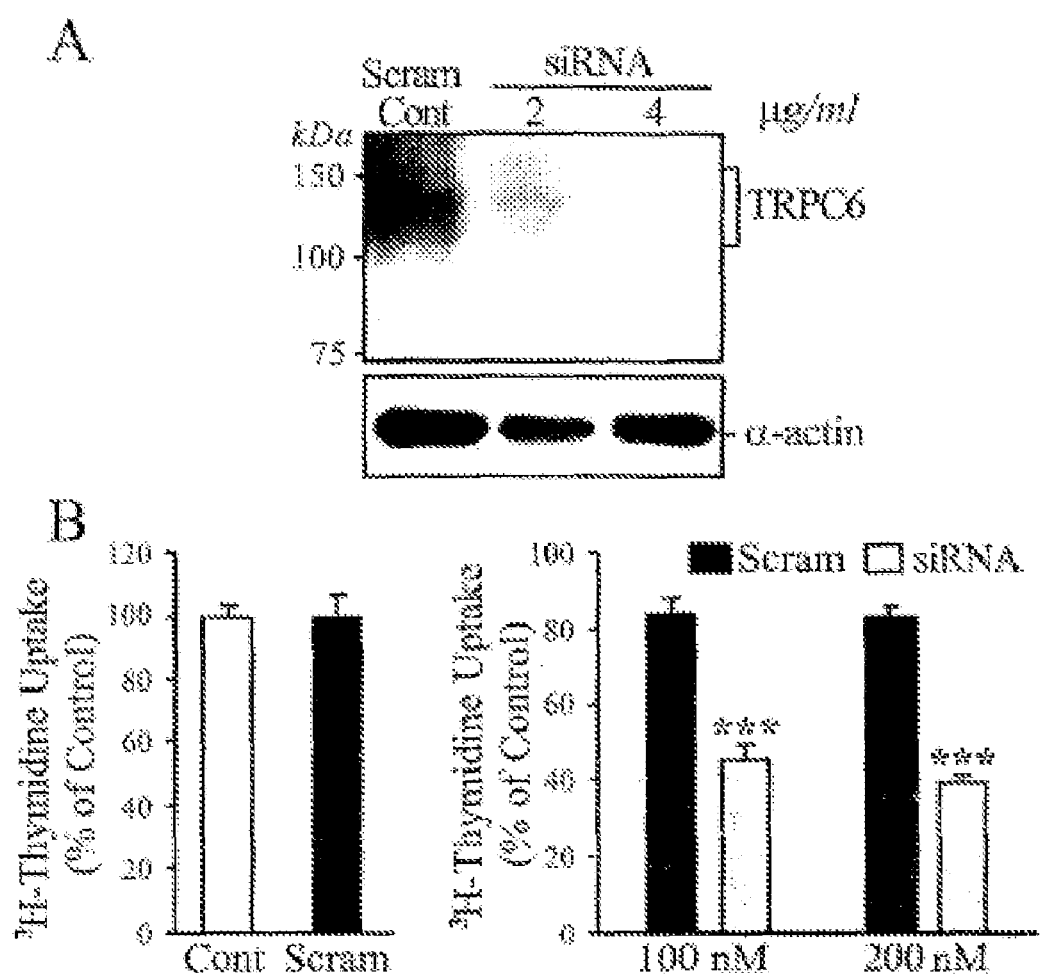

FIG. 8. TRPC6 siRNA attenuates TRPC6 expression and proliferation in IPAH cells. (A) Effect of two concentrations of TRPC6-siRNA-2 expression vector, and its scrambled control (4 µg/ml), on TRPC6 protein expression. (B) Left panel: Normalized [$^3$H]-thymidine uptake plotted for cells untreated (Cont) or treated with the scrambled siRNA duplex (Scram, 200 nM). Right panel: Cell growth in cells transfected with two concentrations of either the scrambled (n=8) or the TRPC6 (n=8) siRNA duplexes. Data are normalized to the basal [$^3$H]-thymidine uptake in the absence of siRNA (Cont). (***, P<0.001 versus Scram)

DETAILED DESCRIPTION

Abbreviations and Definitions

To facilitate understanding of the invention, a number of terms and abbreviations as used herein are defined below as follows:

Bind, Binds or Interacts With: As used herein, "bind," "binds," or "interacts with" refers to that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

Controlled-Release Component: As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

Fragment: As used herein, a "fragment" of a TRPC6 polynucleotide is a portion of a TRPC6 polynucleotide that is less than full-length and comprises at least a minimum length capable of hybridizing specifically with a full-length TRPC6 polynucleotide under stringent hybridization conditions. In certain embodiments, the length of such a fragment can be at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides of a native TRPC6 nucleic acid. A "fragment" of a TRPC6 polypeptide is a portion of a TRPC6 polypeptide that is less than full-length (e.g., a polypeptide consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300 or more amino acids of a native TRPC6 protein or a TRPC6 protein expressed by a polynucleotide having a SNP at −254 of SEQ ID NO: 2), and which can retain at least one functional activity of a full-length TRPC6 polypeptide.

IPAH: As used herein, the term "IPAH" refers to the disorder idiopathic pulmonary arterial hypertension, which in turn broadly refers to disorders in which a subject has an elevated blood pressure in the pulmonary artery that conveys blood from the right ventricle to the lungs due to hypertrophy and/or hyperplasia in the arterial wall.

Protein or Polypeptide: As used herein, the terms "protein" or "polypeptide" mean any peptide-linked chain of amino acids, regardless of length or post-translational modification, e.g., glycosylation or phosphorylation. A "purified" polypeptide is one that is substantially separated from other polypeptides in a cell or organism in which the polypeptide naturally occurs (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% free of contaminants).

Pharmaceutically Acceptable: As used herein, the term "pharmaceutically acceptable" means approved by a regulatory agency of the Federal or a state government or listed in the U.S. Pharmacopeia, incorporated herein by reference in its entirety, or other generally recognized pharmacopeia for use in animals, and more particularly in humans.

Pharmaceutically Acceptable Carrier: As used herein, the term "pharmaceutically acceptable carrier" refers to a diluent, adjuvant, excipient, or vehicle with which a compound is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A compound, if desired, can also combine minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

Pharmaceutically Acceptable Salt: As used herein, the term "pharmaceutically acceptable salt" includes those salts of a pharmaceutically acceptable compound formed with free amino groups such as those derived from hydrochloric, phosphoric, acetic, oxalic, tartaric acids, and those formed with free carboxyl groups such as those derived from sodium, potassium, ammonium, calcium, ferric hydroxides, isopropylamine, triethylamine, 2-ethylamino ethanol, histidine, and procaine. If the compound is basic, salts may be prepared from pharmaceutically acceptable non-toxic acids including inorganic and organic acids. Such acids include acetic, benzene-sulfonic (besylate), benzoic; camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. If the compound is acidic, salts may be prepared from pharmaceutically acceptable organic and inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc. Methods for synthesizing such salts are known to those of skill in the art.

Pro-drug: As used herein, the term "pro-drug" refers to any compound which releases an active drug in vivo when such a compound is administered to a mammalian subject. Pro-drugs can be prepared, for example, by functional group modification of an active drug. The functional group may be cleaved in vivo to release the active drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

Sequence Identity: As used herein, "sequence identity" refers to the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 9 positions in a sequence 10 nucleotides in length are identical to the corresponding positions in a second 10-nucleotide sequence, then the two sequences have 90% sequence identity. Percent sequence identity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

siRNA: As used herein, the term "siRNA" refers to a short-interfering ribonucleic acid which is a polynucleotide having the ability to suppress gene expression through a highly regulated enzyme-mediated process called RNA interference described more fully in the RNAi section below.

SNP-Specific Antibody: By the term "SNP-specific antibody" refers to an antibody (Ab) that binds a protein, polypeptide fragment or polypeptide variant expressed by a polynucleotide having a SNP at −254 of SEQ ID NO: 2 and displays no substantial binding to other naturally occurring proteins other than those sharing the same antigenic determinants as the protein, polypeptide fragment or polypeptide variant expressed by a polynucleotide having a SNP at −254 of SEQ ID NO: 2. The term includes polyclonal and monoclonal Abs as well as Ab fragments.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition related to IPAH. More specific embodiments are included in the Pharmaceutical Preparations and Methods of Administration section below.

Treatment, Treat or Treating: As used herein, the term "treatment," "treating," or "treating" is broadly defined to refer to the prophylaxis, reversal, inhibition, alleviation of symptoms, cure, prognosis, diagnostic analysis, and tempering of a disease, illness, disorder, group of disorders or sickness related to IPAH.

TRPC6 Gene, Polynucleotide, Nucleic Acid or Target: As used herein, the terms "TRPC6 gene," "TRPC6 polynucle-otide," "TRPC6 nucleic acid," or "target," is meant a polynucleotide corresponding to SEQ ID NO: 2 and the related nucleic acids described in the Nucleic Acids Encoding TRPC6 Proteins section below.

TRPC6 Marker: As used herein, a "TRPC6 marker" is any molecule whose presence in a sample (e.g., a cell) indicates that a TRPC6 gene is expressed in the sample. TRPC6 markers include TRPC6 polynucleotides and TRPC6 polypeptides. "Expressing a TRPC6 gene" or like phrases mean that a sample contains a transcription product (e.g., mRNA) of a TRPC6 gene or a translation product of a TRPC6 protein-encoding polynucleotide (e.g., a TRPC6 polypeptide). A cell expresses a TRPC6 gene when it contains a detectable level of a TRPC6 polynucleotide or a TRPC6 polypeptide.

TRPC6 Protein or Polypeptide: By the terms "TRPC6 protein" or "TRPC6 polypeptide" is meant an expression product of a TRPC6 gene such as the native TRPC6 protein, or a protein that shares at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% amino acid sequence identity with one of the foregoing and displays a functional activity of a native TRPC6 protein. A "functional activity" of a protein is any activity associated with the physiological function of the protein or a protein expressed by a polynucleotide having a SNP at −254 of SEQ ID NO: 2. For example, functional activities of a native TRPC6 protein may include transient receptor potential channel activity, particularly inhibition of NF-κB.

Vector: As used herein, the term "vector" refers to a nucleic acid molecule capable of transporting another nucleic acid to which it has been linked. For example, a vector can be an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors."

Regulating Expression of Transient Receptor Potential Channel Genes

The present invention discloses a novel mammalian gene that comprises a mammalian single nucleotide polymorphism (SNP) and the uses of such gene, or fragments thereof, in the characterization, diagnosis, treatment, and prevention of illness, particularly IPAH and associated diseases, disorders and conditions described below. Also provided are polynucleotides and polypeptides encoded by the polynucleotides of the invention. In addition, compositions which interfere with the expression of the polynucleotides above, such as siRNAs, ribozymes, antisense molecules and triplex forming molecules are provided.

Many embodiments of the invention are provided through well known protocols established in the art. For example, the following references provide multiple protocols which may be adapted for use with TRPC6 and a SNP present at a position corresponding to position −254 in SEQ ID NO: 2: Sambrook et al. (1989) Molecular Cloning—A Laboratory Manual (2nd ed.) Vol. 1-3, Cold Spring Harbor Laboratory, Cold Spring Harbor Press, N.Y., ("Sambrook"); and Current Protocols in Molecular Biology, F. M. Ausubel et al., eds., Current Protocols, a joint venture between Greene Publishing Associates, Inc. and John Wiley & Sons, Inc., (e.g., current Nucleic Acids Encoding TRPC6 Proteins Examples of nucleic acid molecules which can be used in certain embodiments include the native TRPC6 polynucleotide and deposited with GenBank as Accession No. NM_004621 (SEQ ID NO: 2; mRNA) which expresses a polypeptide having GenBank Accession No. NP_004612 (SEQ ID NO: 3; protein; also described as GenBank Accession No. CAC01684). Various fragments, variants, analogs, and homologs can be used in certain aspects.

In certain embodiments, nucleic acid molecules may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes a native TRPC6 protein may be identical to the nucleotide sequence of SEQ ID NO: 2 or it may also be a different coding sequence which, as a result of the redundancy or degeneracy of the genetic code, encodes the same polypeptide as the polynucleotides of SEQ ID NO: 2. Examples of nucleotide codons which provide the same expressed amino acid are summarized in Table 1:

TABLE 1

| Codon | Full Name | Abbreviation (3 Letter) | Abbreviation (1 Letter) |
|---|---|---|---|
| TTT | Phenylalanine | Phe | F |
| TTC | Phenylalanine | Phe | F |
| TTA | Leucine | Leu | L |
| TTG | Leucine | Leu | L |
| TCT | Serine | Ser | S |
| TCC | Serine | Ser | S |
| TCA | Serine | Ser | S |
| TCG | Serine | Ser | S |
| TAT | Tyrosine | Tyr | Y |
| TAC | Tyrosine | Tyr | Y |
| TAA | Termination | Ter | X |
| TAG | Termination | Ter | X |
| TGT | Cysteine | Cys | C |
| TGC | Cysteine | Cys | C |
| TGA | Termination | Ter | X |
| TGG | Tryptophan | Trp | W |
| CTT | Leucine | Leu | L |
| CTC | Leucine | Leu | L |
| CTA | Leucine | Leu | L |
| CTG | Leucine | Leu | L |
| CCT | Proline | Pro | P |
| CCC | Proline | Pro | P |
| CCA | Proline | Pro | P |
| CCG | Proline | Pro | P |
| CAT | Histidine | His | H |
| CAC | Histidine | His | H |
| CAA | Glutamine | Gln | Q |
| CAG | Glutamine | Gln | Q |
| CGT | Arginine | Arg | R |
| CGC | Arginine | Arg | R |
| CGA | Arginine | Arg | R |
| CGG | Arginine | Arg | R |
| ATT | Isoleucine | Ile | I |
| ATC | Isoleucine | Ile | I |
| ATA | Isoleucine | Ile | I |
| ATG | Methionine | Met | M |
| ACT | Threonine | Thr | T |
| ACC | Threonine | Thr | T |
| ACA | Threonine | Thr | T |
| ACG | Threonine | Thr | T |
| AAT | Asparagine | Asn | N |
| AAC | Asparagine | Asn | N |
| AAA | Lysine | Lys | K |
| AAG | Lysine | Lys | K |
| AGT | Serine | Ser | S |
| AGC | Serine | Ser | S |
| AGA | Arginine | Arg | R |
| AGG | Arginine | Arg | R |
| GTT | Valine | Val | V |
| GTC | Valine | Val | V |
| GTA | Valine | Val | V |
| GTG | Valine | Val | V |
| GCT | Alanine | Ala | A |
| GCC | Alanine | Ala | A |
| GCA | Alanine | Ala | A |
| GCG | Alanine | Ala | A |
| GAT | Aspartate | Asp | D |
| GAC | Aspartate | Asp | D |
| GAA | Glutamate | Glu | E |
| GAG | Glutamate | Glu | E |
| GGT | Glycine | Gly | G |
| GGC | Glycine | Gly | G |
| GGA | Glycine | Gly | G |
| GGG | Glycine | Gly | G |

Other nucleic acid molecules can be variants of the native TRPC6 gene such as those that encode fragments, analogs and derivatives of a native TRPC6 protein. Such variants may be, e.g., a naturally occurring allelic variant of the native TRPC6 gene, a homolog of the native TRPC6 gene, or a non-naturally occurring variant of the native TRPC6 gene. Specifically included is a TRPC6 gene having a SNP at −254 of SEQ ID NO: 2. Such a variant can also include the A-361T and C-218T SNPs either individually or in any combination. A fragment, for example could be a polynucleotide of the sequence or comprising the sequence of SEQ ID NO: 4. Analogs and derivatives of a TRPC6 gene could also be of or comprise a sequence of SEQ ID NO: 4. These variants have a nucleotide sequence that differs from the native TRPC6 gene in one or more bases. For example, the nucleotide sequence of such variants can feature a deletion, addition, or substitution of one or more nucleotides of the native TRPC6 gene. Nucleic acid insertions can be from about 1 to 10 contiguous nucleotides, and deletions from about 1 to 30 contiguous nucleotides.

In other applications, variant TRPC6 proteins displaying substantial changes in structure can be generated by making nucleotide substitutions that cause less than conservative changes in the encoded polypeptide. Examples of such nucleotide substitutions, as shown in Table 1, are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine. Table 2 provides similar possible substitution possibilities:

TABLE 2

| Amino Acid | 3-letter code | 1-letter code | Properties |
|---|---|---|---|
| Alanine | Ala | A | Aliphatic, hydrophobic, neutral |
| Arginine | Arg | R | polar, hydrophilic, charged (+) |

TABLE 2-continued

| Amino Acid | 3-letter code | 1-letter code | Properties |
| --- | --- | --- | --- |
| Asparagine | Asn | N | polar, hydrophilic, neutral |
| Aspartate | Asp | D | polar, hydrophilic, charged (−) |
| Cysteine | Cys | C | polar, hydrophobic, neutral |
| Glutamine | Gln | Q | polar, hydrophilic, neutral |
| Glutamate | Glu | E | polar, hydrophilic, charged (−) |
| Glycine | Gly | G | aliphatic, neutral |
| Histidine | His | H | aromatic, polar, hydrophilic, charged (+) |
| Isoleucine | Ile | I | aliphatic, hydrophobic, neutral |
| Leucine | Leu | L | aliphatic, hydrophobic, neutral |
| Lysine | Lys | K | polar, hydrophilic, charged (+) |
| Methionine | Met | M | hydrophobic, neutral |
| Phenylalanine | Phe | F | aromatic, hydrophobic, neutral |
| Proline | Pro | P | hydrophobic, neutral |
| Serine | Ser | S | polar, hydrophilic, neutral |
| Threonine | Thr | T | polar, hydrophilic, neutral |
| Tryptophan | Trp | W | aromatic, hydrophobic, neutral |
| Tyrosine | Tyr | Y | aromatic, polar, hydrophobic |
| Valine | Val | V | aliphatic, hydrophobic, neutral |

Naturally occurring allelic variants of a native TRPC6 gene, such as, for example, the native TRPC6 gene having a SNP at −254 of SEQ ID NO: 2, or native TRPC6 mRNAs can be nucleic acids isolated from human tissue that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native TRPC6 gene or native TRPC6 mRNAs, and encode polypeptides having structural similarity to a native TRPC6 protein. Homologs of the native TRPC6 gene or native TRPC6 mRNAs can be nucleic acids isolated from other species that have at least 75% (e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native TRPC6 gene or native TRPC6 mRNAs, and encode polypeptides having structural similarity to native TRPC6 protein. Public and/or proprietary nucleic acid databases can be searched to identify other nucleic acid molecules having a high percent (e.g., 75, 85, 95% or more) sequence identity to the native TRPC6 gene or native TRPC6 mRNAs.

Non-naturally occurring TRPC6 gene or mRNA variants are nucleic acids that do not occur in nature (e.g., are made by the hand of man), have at least 75% (e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native TRPC6 gene or native TRPC6 mRNAs, and encode polypeptides having structural similarity to native TRPC6 protein. Examples of non-naturally occurring TRPC6 gene variants are those that encode a fragment of a TRPC6 protein, those that hybridize to the native TRPC6 gene or a complement of the native TRPC6 gene under stringent conditions, those that share at least 65%, 66%, 67%, 68%, 69%, 70%, 71%, 72%, 73%, or 74% sequence identity with the native TRPC6 gene or a complement thereof, and those that encode a TRPC6 fusion protein.

Nucleic acids encoding fragments of a native TRPC6 protein can be those that encode, e.g., 2, 3, 4, 5, 10, 25, 50, 100, 150, 200, 250, 300, or more amino acid residues of the native TRPC6 protein. Shorter oligonucleotides (e.g., those of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 100, 125, 150 or 200 base pairs in length) that encode or hybridize with nucleic acids that encode fragments of a native TRPC6 protein can be used as probes, primers, or antisense molecules. Longer polynucleotides (e.g., those of 300, 400, 500, 600, 700, 800, 900, 1000, 1100, 1200, 1300, 1400, 1500, 1600, 1700, 1800, 1900 or 2000 base pairs) that encode or hybridize with nucleic acids that encode fragments of a native TRPC6 protein can also be used in various aspects. Nucleic acids encoding fragments of a native TRPC6 protein can be made by enzymatic digestion (e.g., using a restriction enzyme) or chemical degradation of the full length native TRPC6 gene, a TRPC6 mRNA or cDNA, or variants of the foregoing.

Nucleic acids that hybridize under stringent conditions to the nucleic acid of SEQ ID NO: 2 or the complement of SEQ ID NO: 2 can also be used. See Ausubel and Sambrook, supra. For example, such nucleic acids can be those that hybridize to SEQ ID NO: 2 or the complement of SEQ ID NO: 2 under low stringency conditions, moderate stringency conditions, or high stringency conditions are contemplated in certain embodiments. In other embodiments, such nucleotide acids are those having a nucleotide sequence that is the complement of all or a portion of SEQ ID NO: 2. Other variants of the native TRPC6 gene can be polynucleotides that share at least 65% (e.g., 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity to SEQ ID NO: 2 or the complement of SEQ ID NO: 2. Nucleic acids that hybridize under stringent conditions to or share at least 65% sequence identity with SEQ ID NO: 2 or the complement of SEQ ID NO: 2 can be obtained by techniques known in the art such as by making mutations in the native TRPC6 gene, or by isolation from an organism expressing such a nucleic acid (e.g., an allelic variant). See Ausubel and Sambrook, supra.

Other embodiments include nucleic acid molecules encoding TRPC6 fusion proteins. Such nucleic acids can be made by preparing a construct (e.g., an expression vector) that expresses a TRPC6 fusion protein when introduced into a suitable host. For example, such a construct can be made by ligating a first polynucleotide encoding a TRPC6 protein fused in frame with a second polynucleotide encoding another protein such that expression of the construct in a suitable expression system yields a fusion protein.

The nucleic acid molecules can be modified at a base moiety, sugar moiety; or the phosphate backbone, e.g., to improve stability of the molecule, hybridization, and the like. For example the nucleic acid molecules can be conjugated to groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents (see, e.g., Zon (1988) Pharm. Res. 5:539-549).

TRPC6 Proteins

In some embodiments, a purified TRPC6 protein encoded by a nucleic acid of the invention is contemplated. TRPC6 protein can be a purified native TRPC6 protein that has the deduced amino acid sequence of SEQ ID NO: 3. Variants of native TRPC6 proteins such as fragments, analogs and derivatives of native TRPC6 proteins are also contemplated. Such variants include, e.g., a polypeptide encoded by a naturally occurring allelic variant of a native TRPC6 gene, such as, for example, the native TRPC6 gene having a SNP at −254 of SEQ ID NO: 2, a polypeptide encoded by an alternative splice form of a native TRPC6 gene, a polypeptide encoded by a homolog of a native TRPC6 gene, and a polypeptide encoded by a non-naturally occurring variant of a native TRPC6 gene.

TRPC6 protein variants have a peptide sequence that differs from a native TRPC6 protein in one or more amino acids. The peptide sequence of such variants can feature a deletion, addition, or substitution of one or more amino acids of a native TRPC6 polypeptide. Amino acid insertions can be from about 1, 2, 3, and 4 to 5 contiguous amino acids, and deletions can be from about 1, 2, 3, 4, 5, 6, 7, 8, and 9 to 10 contiguous amino acids. In some applications, variant TRPC6 proteins substantially maintain a native TRPC6 protein functional activity (e.g., transient receptor potential channel activity, particularly inhibition of NF-κB). For other applications, variant TRPC6 proteins lack or feature a significant reduction in a TRPC6 protein functional activity. Where it is desired to retain a functional activity of native TRPC6 protein, TRPC6 protein variants can be made by expressing nucleic acid molecules that feature silent or conservative changes. Variant TRPC6 proteins with substantial changes in functional activity can be made by expressing nucleic acid molecules that feature less than conservative changes.

TRPC6 protein fragments corresponding to one or more particular motifs and/or domains or to arbitrary sizes, for example, can be of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 120, 130, 140, 150, 160, 170, 180, 190, 200, 210, 220, 230, 240, 250, 260, 270, 280, 290, 300 or more amino acids in length. Isolated peptidyl portions of TRPC6 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a TRPC6 protein can be arbitrarily divided into fragments of desired length with no overlap of the fragments, or divided into overlapping fragments of a desired length. The fragments can be produced (recombinantly or by chemical synthesis) and tested to identify those peptidyl fragments which can function as either agonists or antagonists of a native TRPC6 protein or, for example, a protein expressed by the native TRPC6 gene having a SNP at −254 of SEQ ID NO: 2.

Another embodiment provides recombinant forms of the TRPC6 proteins. Recombinant polypeptides can be, in addition to native TRPC6 protein, encoded by a nucleic acid that has at least 85% sequence identity (e.g., 85%, 86%, 87%, 88%, 89%, 90%, 91%, 92%, 93%, 94%, 95%, 96%, 97%, 98%, and 99%) with the nucleic acid sequence of SEQ ID NO: 2. In an embodiment, variant TRPC6 proteins have one or more functional activities of native TRPC6 protein.

TRPC6 protein variants can be generated through various techniques known in the art. For example, TRPC6 protein variants can be made by mutagenesis, such as by introducing discrete point mutation(s), or by truncation. Mutation can give rise to a TRPC6 protein variant having substantially the same, or merely a subset of the functional activity of a native TRPC6 protein. Alternatively, antagonistic forms of the protein can be generated which are able to inhibit the function of the naturally occurring form of the protein, such as by competitively binding to another molecule that interacts with TRPC6 protein. In addition, agonistic forms of the protein may be generated that constitutively express on or more TRPC6 functional activities. Other variants of TRPC6 proteins that can be generated include those that are resistant to proteolytic cleavage, as for example, due to mutations which alter protease target sequences. Whether a change in the amino acid sequence of a peptide results in a TRPC6 protein variant having one or more functional activities of a native TRPC6 protein can be readily determined by testing the variant for a native TRPC6 protein functional activity.

As another example, TRPC6 protein variants can be generated from a degenerate oligonucleotide sequence. Chemical synthesis of a degenerate gene sequence can be carried out in an automatic DNA synthesizer, and the synthetic genes then ligated into an appropriate expression vector. One purpose for a degenerate set of genes is to provide, in one mixture, all of the sequences encoding the desired set of potential TRPC6 protein sequences. The synthesis of degenerate oligonucleotides is well known in the art (see, e.g., Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, e.g., Scott et al. (1990) Science 249:386-390; Roberts et al. (1992) Proc. Natl. Acad. Sci. USA 89:2429-2433; Devlin et al. (1990) Science 249: 404-406; Cwirla et al. (1990) Proc. Natl. Acad. Sci. USA 87: 6378-6382; as well as U.S. Pat. Nos. 5,223,409; 5,198,346; and 5,096,815).

Similarly, a library of coding sequence fragments can be provided for a TRPC6 gene clone in order to generate a variegated population of TRPC6 protein fragments for screening and subsequent selection of fragments having one or more native TRPC6 protein functional activities. A variety of techniques are known in the art for generating such libraries, including chemical synthesis. In one embodiment, a library of coding sequence fragments can be generated by (i) treating a double-stranded PCR fragment of a TRPC6 gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of TRPC6 gene variants. The most widely used techniques for screening large gene libraries typically involve cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins, e.g., in the order of $10^{26}$ molecules. For example, a library of TRPC6 variants can be created and screened by the methods provided in Shin et al., "Combinatorial Solid Phase Peptide Synthesis and Bioassays," J. Biochem. and Mol. Biol. 38:5 517-525 (2005), incorporated herein by reference in its entirety. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. See, for example, Arkin and Yourvan (1992) Proc. Natl. Acad. Sci. USA 89:7811-7815; Yourvan et al. (1992) Parallel Problem Solving from NATURE, Maenner and Manderick, eds., Elsevier Publishing Co., Amsterdam, pp. 401-410; Delgrave et al. (1993) Protein Engineering 6(3): 327-331.

Also provided for reduction of TRPC6 proteins to generate mimetics, e.g. peptide or non-peptide agents, that are able to disrupt binding of a TRPC6 protein to other proteins or molecules with which the native TRPC6 protein interacts. Thus, the mutagenic techniques described herein can also be used to map which determinants of TRPC6 protein participate in the intermolecular interactions involved in, e.g., binding of a TRPC6 protein to other proteins which may function upstream (e.g., activators or repressors of TRPC6 functional activity) of the TRPC6 protein or to proteins or nucleic acids which may function downstream of the TRPC6 protein, and whether such molecules are positively or negatively regulated by the TRPC6 protein. To illustrate, the critical residues of a TRPC6 protein which are involved in molecular recognition of, e.g., the TRPC6 protein or other components upstream or downstream of the TRPC6 protein can be determined and used to generate TRPC6 protein-derived peptidomimetics which competitively inhibit binding of the TRPC6 protein to that moiety. By employing scanning mutagenesis to map the amino acid residues of a TRPC6 protein that are involved in binding other extracellular proteins, peptidomimetic compounds can be generated which mimic those residues of a native TRPC6 protein. Such mimetics may then be used to interfere with the normal function of a TRPC6 protein.

For example, non-hydrolyzable peptide analogs of such residues can be generated using benzodiazepine (see, e.g., Freidinger et al. in PEPTIDES: CHEMISTRY AND BIOLOGY, G. R. Marshall ed., ESCOM Publisher: Leiden, Netherlands, 1988), azepine (e.g., see Huffman et al. in PEPTIDES: CHEMISTRY AND BIOLOGY, G. R. Marshall ed., ESCOM Publisher: Leiden, Netherlands, 1988), substituted gamma lactam rings (Garvey et al. in PEPTIDES: CHEMISTRY AND BIOLOGY, G. R. Marshall ed., ESCOM Publisher: Leiden, Netherlands, 1988), keto-methylene pseudopepitides (Ewenson et al. (1986) J. Med. Chem. 29:295; and Ewenson et al. in PEPTIDES: STRUCTURE AND FUNCTION (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134:71). TRPC6 proteins may also be chemically modified to create TRPC6 protein derivatives by forming covalent or aggregate conjugates with other chemical moieties, such as glycosyl groups, lipids, phosphate, acetyl groups and the like. Covalent derivatives of TRPC6 protein can be prepared by linking the chemical moieties to functional groups on amino acid side chains of the protein or at the N-terminus or at the C-terminus of the polypeptide.

Methods of producing TRPC6 polypeptides and full-length proteins are also contemplated. For example, a host cell transfected with a vector able to direct expression of a nucleotide sequence encoding the subject polypeptides can be cultured under appropriate conditions to induce expression of the polypeptides by the cells. The cells may then be harvested, lysed, and the protein isolated. A recombinant TRPC6 protein can be isolated from host cells using techniques known in the art for purifying proteins, including ion-exchange chromatography, gel filtration chromatography, ultrafiltration, electrophoresis, and immunoaffinity purification.

An example of isolating a recombinant TRPC6 protein by immunoaffinity purification would involve immobilization of an anti-TRPC6 Ab on a column chromatography matrix. Such a matrix can then be used to purify the TRPC6 protein from cell lysates (see, e.g., Ausubel et al., supra). After immunoaffinity chromatography, the TRPC6 protein may be further purified using techniques known in the art, such as high performance liquid chromatography (see, e.g., Fisher, Laboratory Techniques In Biochemistry And Molecular Biology, Work and Burdon, eds., Elsevier, 1980). In some embodiments, a TRPC6 protein is expressed as a fusion protein containing an affinity tag (e.g., GST) to facilitate its purification.

Conjugates

Another modification of the nucleic acids herein involves chemically linking to the nucleic acid one or more moieties or conjugates which enhance the activity, cellular distribution or cellular uptake of the nucleic acid. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of nucleic acids. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties can include groups that improve uptake, enhance resistance to degradation, and/or strengthen sequence-specific hybridization with the target nucleic acid. Groups that enhance the pharmacokinetic properties can include groups that improve uptake, distribution, metabolism or excretion of the compounds described herein.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glyc-ero-3-H-phosphonate, a polyamine or a polyethylene glycol chain, or adamantane acetic acid, a palmityl moiety, or an octadecylamine or hexylamino-carbonyl-oxycholesterol moiety. Nucleic acids can also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Antisense, Ribozyme, Triplex Techniques

Another aspect relates to the use of purified antisense nucleic acids to inhibit expression of TRPC6 polypeptides. Antisense nucleic acid molecules can include those that specifically hybridize (e.g., bind) under cellular conditions to cellular mRNA and/or genomic DNA encoding a TRPC6 polynucleotide in a manner that inhibits expression of the TRPC6 polypeptide, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes a TRPC6 polypeptide. Alternatively, the antisense construct can take the form of an oligonucleotide probe generated ex vivo which, when introduced into an TRPC6 polypeptide expressing cell, causes inhibition of TRPC6 polypeptide expression by hybridizing with an mRNA and/or genomic sequences coding for TRPC6 polypeptide. Such oligonucleotide probes can be modified oligonucleotides that are resistant to endogenous nucleases, e.g., exonucleases and/or endonucleases; and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958-976; and Stein et al. (1988) Cancer Res 48:2659-2668. With respect to antisense DNA, oligodeoxyribonucleotides can be derived from the translation initiation site, e.g., between the −10 and +10 regions of a TRPC6 polypeptide encoding nucleotide sequence.

Antisense approaches involve the design of oligonucleotides (either DNA or RNA) that are complementary to TRPC6 mRNA. The antisense oligonucleotides will bind to TRPC6 mRNA transcripts and prevent translation. Absolute complementarity is not required. The ability to hybridize will depend on both the degree of complementarity and the length of the antisense nucleic acid. Generally, the longer the hybridizing nucleic acid, the more base mismatches with an RNA it may contain and still form a stable duplex or triplex. One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. Wagner, R. Nature 372:333 (1994). Therefore, oligonucleotides complementary to either the 5' or 3' untranslated, non-coding regions of a TRPC6 gene could be used in an antisense approach to inhibit translation of endogenous TRPC6 mRNA. Oligonucleotides complementary to the 5' untranslated region of the mRNA can include the complement of the AUG start codon. Although antisense oligonucleotides complementary to mRNA coding regions are generally less efficient inhibitors of translation, these could still be used. Whether designed to hybridize to the 5', 3' or coding region of TRPC6 mRNA, antisense nucleic acids can be less that about 100 (e.g., less than about 30, 29, 28, 27, 26, 25, 24, 23, 22, 21, 20, 19 or 18) nucleotides in length. Generally, in order to be effective, the antisense oligonucleotide could be 18 or more nucleotides in length, but may be shorter depending on the conditions.

Specific antisense oligonucleotides can be tested for effectiveness using in vitro studies to assess the ability of the antisense oligonucleotide to inhibit gene expression. Such studies can (1) utilize controls (e.g., a non-antisense oligonucleotide of the same size as the antisense oligonucleotide) to distinguish between antisense gene inhibition and nonspecific biological effects of oligonucleotides, and (2) compare levels of the target RNA or protein with that of an internal control RNA or protein.

In certain aspects, antisense oligonucleotides can include at least one modified base or sugar moiety such as those provided above. Antisense oligonucleotides can also be an alpha-anomeric oligonucleotide.

Oligonucleotides can be synthesized by standard methods known in the art, e.g., by use of an automated DNA synthesizer, as described in Ausubel and Sambrook. Phosphorothioate oligonucleotides may be synthesized by the method of Stein et al. (1988) Nucl. Acids Res. 16:3209. Methylphosphonate oligonucleotides can be prepared by use of controlled pore glass polymer supports (e.g., as described in Sarin et al. (1988) Proc. Natl. Acad. Sci. U.S.A. 85:7448-7451).

Certain embodiment also provide methods for delivering one or more of the above-described nucleic acid molecules into cells that express TRPC6 protein. A number of methods have been developed for delivering antisense DNA or RNA into cells. For example, antisense molecules can be introduced directly into a cell by electroporation, liposome-mediated transfection, CaCl-mediated transfection, or using a gene gun. Modified nucleic acid molecules designed to target the desired cells (e.g., antisense oligonucleotides linked to peptides or Abs that specifically bind receptors or antigens expressed on the target cell surface) can be used. To achieve high intracellular concentrations of antisense oligonucleotides (as may be required to suppress translation on endogenous mRNAs), an exemplary approach utilizes a recombinant DNA construct in which the antisense oligonucleotide is placed under the control of a strong promoter (e.g., the CMV promoter).

Ribozymes

Ribozyme molecules designed to catalytically cleave TRPC6 mRNA transcripts can also be used to prevent translation of TRPC6 mRNAs and expression of TRPC6 proteins. As one example, hammerhead ribozymes that cleave mRNAs at locations dictated by flanking regions that form complementary base pairs with the target mRNA might be used so long as the target mRNA has the following common sequence: 5'-UG-3'. As another example, hairpin and hepatitis delta virus ribozymes may also be used. To increase efficiency and minimize the intracellular accumulation of non-functional mRNA transcripts, a ribozyme should be engineered so that the cleavage recognition site is located near the 5' end of the target TRPC6 mRNA. Ribozymes can be delivered to a cell using a vector as described below.

Other methods can also be used to reduce TRPC6 gene expression in a cell. For example, TRPC6 gene expression can be reduced by inactivating or "knocking out" the TRPC6 gene or its promoter using targeted homologous recombination. See, e.g., Kempin et al., Nature 389: 802 (1997); Smithies et al. (1985) Nature 317:230-234; Thomas and Capecchi (1987) Cell 51:503-512; and Thompson et al. (1989) Cell 5:313-321. For example, a mutant, non-TRPC6 gene variant (or a completely unrelated DNA sequence) flanked by DNA homologous to the endogenous TRPC6 gene (either the coding regions or regulatory regions of the TRPC6 gene) can be used, with or without a selectable marker and/or a negative selectable marker, to transfect cells that express TRPC6 protein in vivo.

TRPC6 gene expression might also be reduced by targeting deoxyribonucleotide sequences complementary to the regulatory region of the TRPC6 gene (i.e., the TRPC6 promoter and/or enhancers) to form triple helical structures that prevent transcription of the TRPC6 gene in target cells. See generally, Helene, C. (1991) Anticancer Drug Des. 6(6): 569-84; Helene, C., et al. (1992) Ann. N.Y. Acad. Sci. 660:27-36; and Maher, L. J. (1992) Bioassays 14(12): 807-15. Nucleic acid molecules to be used in this technique can be single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

In certain aspects, antisense RNA and DNA, ribozyme, and triple helix molecules can be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

RNA Interference (RNAi)

The use of short-interfering RNA (siRNA) is a technique known in the art for inhibiting expression of a target gene by introducing exogenous RNA into a living cell (Elbashir et al. 2001. Nature. 411:494-498). siRNAs suppress gene expression through a highly regulated enzyme-mediated process called RNA interference (RNAi). RNAi involves multiple RNA-protein interactions characterized by four major steps: assembly of siRNA with the RNA-induced silencing complex (RISC), activation of the RISC, target recognition and target cleavage. Therefore, identifying siRNA-specific features likely to contribute to efficient processing at each step is beneficial efficient RNAi. Reynolds et al. provide methods for identifying such features. A. Reynolds et al., "Rational siRNA design for RNA interference", Nature Biotechnology 22(3), March 2004. In that study, eight characteristics associated with siRNA functionality were identified: low G/C content, a bias towards low internal stability at the sense strand 3'-terminus, lack of inverted repeats, and sense strand base preferences (positions 3, 10, 13 and 19). Further analyses revealed that application of an algorithm incorporating all eight criteria significantly improves potent siRNA selection. siRNA sequences that contain internal repeats or palindromes may form internal fold-back structures. These hairpin-like structures may exist in equilibrium with the duplex form, reducing the effective concentration and silencing potential of the siRNA. The relative stability and propensity to form internal hairpins can be estimated by the predicted melting temperatures ($T_M$). Sequences with high Tm values would favor internal hairpin structures.

siRNA can be used either ex vivo or in vivo, making it useful in both research and therapeutic settings. Unlike in other antisense technologies, the RNA used in the siRNA technique has a region with double-stranded structure that is made identical to a portion of the target gene, thus making inhibition sequence-specific. Double-stranded RNA-mediated inhibition has advantages both in the stability of the material to be delivered and the concentration required for effective inhibition.

The extent to which there is loss of function of the target gene can be titrated using the dose of double stranded RNA delivered. A reduction or loss of gene expression in at least 99% of targeted cells has been shown. See, e.g., U.S. Pat. No. 6,506,559. Lower doses of injected material and longer times after administration of siRNA may result in inhibition in a smaller fraction of cells. Quantitation of gene expression in a cell show similar amounts of inhibition at the level of accumulation of target mRNA or translation of target protein.

The RNA used in this technique can comprise one or more strands of polymerized ribonucleotides, and modification can be made to the sugar-phosphate backbone as disclosed above. The double-stranded structure is often formed using either a single self-complementary RNA strand (hairpin) or two complementary RNA strands. RNA containing a nucleotide sequences identical to a portion of the target gene is preferred for inhibition, although sequences with insertions, deletions, and single point mutations relative to the target sequence can also be used for inhibition. Sequence identity may be optimized using alignment algorithms known in the art and through calculating the percent difference between the nucleotide sequences. The duplex region of the RNA could also be described in functional terms as a nucleotide sequence that is capable of hybridizing with a portion of the target gene transcript.

siRNA can often be a more effective therapeutic tool than other types of gene suppression due to siRNA's potent gene inhibition and ability to target receptors with a specificity can reach down to the level of single-nucleotide polymorphisms. Such specificity generally results in fewer side effects than is seen in conventional therapies, because other genes are not be affected by application of a sufficiently sequence-specific siRNA.

There are multiple ways to deliver siRNA to the appropriate target. Standard transfection techniques may be used, in which siRNA duplexes are incubated with cells of interest and then processed using standard commercially available kits. Electroporation techniques of transfection may also be appropriate. Cells or organisms can be soaked in a solution of the siRNA, allowing the natural uptake processes of the cells or organism to introduce the siRNA into the system. Viral constructs packaged into a viral particle would both introduce the siRNA into the cell line or organism and also initiate transcription through the expression construct. Other methods known in the art for introducing nucleic acids to cells may also be used, including lipid-mediated carrier transport, chemical-mediated transport, such as calcium phosphate, and the like.

For therapeutic uses, tissue-targeted nanoparticles may serve as a delivery vehicle for siRNA. These nanoparticles carry the siRNA exposed on the surface, which is then available to bind to the target gene to be silenced. Schiffelers, et al., Nucleic Acids Research (2004) 32(19):e149. These nanoparticles may be introduced into the cells or organisms using the above described techniques already known in the art. Designing the appropriate nanoparticles for a particular illness is a matter of determining the appropriate targets for the particular disease. In the case of IPAH, the present invention has already revealed potential targets for this powerful therapy.

Delivery Vehicles

Other delivery vehicles for therapeutic uses in humans include pharmaceutical compositions, intracellular injection, and intravenous introduction into the vascular system. Inhibition of gene expression can be confirmed by using biochemical techniques such as RNA solution hybridization, nuclease protection, Northern hybridization, reverse transcription, gene expression monitoring with a microarray, Ab binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression may be assayed using a reporter or drug resistance gene whose protein product can be easily detected and quantified. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. These techniques are well known and easily practiced by those skilled in the art. For in vivo use in humans, reduction or elimination of symptoms of illness will confirm inhibition of the target gene's expression.

As shown in FIG. 1B, SNP-1 comprises a SNP site that is either C or G at nucleotide position −254 relative to the start site ATG. The SNP-1G variant comprises part of a NF-κB transcription factor binding site motif and subjects with this variant on both alleles of the TRPC6 gene have been associated with IPAH (Table 13 and Table 14). The presence of the biallelic SNP-1G variant can be used as a predictor of and predisposition to IPAH prior to the onset of the disorder. A subject having either the biallelic SNP-1G variant or having the heterozygous allele can be treated using siRNA therapy to prevent NF-κB from binding to the promoter region of the TRPC6 gene and thereby prevent or reduce the effect of IPAH. In another embodiment, a subject with IPAH is treated with siRNA therapy to prevent NF-κB from binding to the promoter region of the TRPC6 gene and thereby to prevent or reduce the effect of IPAH.

In another embodiment, a subject with IPAH can be treated with an inhibitor of NF-κB transcription factor binding activity to an NF-κB binding site in a gene promoter or with an inhibitor of translocation of NF-κB into the nucleus or with an inhibitor of NF-κB/IκB dissociation or an inhibitor of IκB phosphorylation. In addition, a subject at risk for IPAH or having IPAH may be treated with a combination of any one of the above schemes together with a treatment with glucocorticoids to prevent NF-κB from binding to the promoter region of the TRPC6 gene and thereby to prevent or reduce the development or effect of IPAH.

As shown in Table 13 and Table 15, the absence of SNP-1G variant on both alleles of the TRPC6 gene is associated with a higher incidence of susceptibility to and a predisposition to SPH and not to susceptibility to and a predisposition to IPAH.

In another embodiment, the polynucleotide corresponding to SEQ ID NO: 2 can be used to prevent an NF-κB transcription factor and/or an NF-κB transcription factor complexed with other factor(s) binding to the 5'UTR of an expressed TRPC6 mRNA molecule, thereby releasing the mRNA molecule for post-transcriptional processing within a biological tissue. The post-transcriptional processing can include, but is not limited to, maturation of mRNA (removal of introns and exon-exon splicing regulated by snRNA(s)), translocation of the mature mRNA from the nucleus to the endoplasmic reticulum, translation of the mRNA, and degradation of the mRNA.

As noted above, induction of inflammatory pathways in, for example, intestinal epithelium and antigen-presenting cells, as well as production of interferons, cytokines, and TNF-α, is known to be mediated by the NF-κB family of transcription factors (Chamaillard et al. (2003) Cell. Microbiol. 5: 581-592). It is possible that induction of such inflammatory responses, albeit undetectable in patients with IPAH, can have infiltrated the pulmonary circulation and thereby induced and exacerbated the symptoms attributed to IPAH.

Another aspect relates to the use of siRNA to inhibit the expression of TRPC6 gene. Human PASMC were isolated and cultured from normal subjects (normal PASMC) and subjects with IPAH (IPAH-PASMC). Levels of canonical TRP (TRPC) isoforms (mRNA and protein) were measured using RT-PCR and Western blot analysis. In addition, levels of TRPC6 in vivo were measured and compared with levels of Ki67, a nuclear protein expressed during S and $G_2$/M phase of the cell cycle, using in situ immunofluorescence staining of proliferating PASMC (see Kuga et al. (1996) Circ. Res. 79:14-19). Cell cycle phase was determined by BrdU uptake and by [$^3$H]-thymidine incorporation into DNA. PASMC were incubated with [$^3$H]-thymidine for 16 hours following 24 hours of growth arrest and 48 hours of growth induction and measuring percent extent of radiolabel incorporation into precipitated DNA.

In separate experiments, siRNA was used to prevent expression and translation of the TRPC6 gene in vitro. Several fragments of open reading frames in the TRPC6 gene were identified which suppressed expression of TRPC6 protein and mRNA levels. One sequence, TRPC6 siRNA-2 (AAGGTCTTTATGCAATTGCTG; SEQ ID NO: 5), was most effective in COS-7 cells and was used to silence the TRPC6 gene in PASMC cell cultures. A scrambled siRNA vector served as a non-silencing control.

All TRPC mRNA transcripts were detected in normal human (NPH) lung tissues; the mRNA expression levels of TRPC1, 4, and 6 exceeded that of TRPC3, 5, and 7 (FIG. 2A). NPH-PASMC (S) highly expressed TRPC1, 4, and 6, whereas pulmonary artery endothelial cells (PAEC; E) highly expressed TRPC1, 3, and 4 (FIG. 2B). PASMC also expressed low levels of TRPC5 and 7. These data suggest that, while TRPC1 and 4 are ubiquitously expressed, TRPC3 and 6 appear to be PAEC- and PASMC-dominant TRPC isoforms, respectively, in normal subjects.

Sixty seven percent of the proliferating (SMGM) PASMC were in the S and $G_2$/M phases and 27% in the $G_0$/$G_1$ phases. In growth-arrested (SMBM) PASMC, 7% of the cells were in the S and $G_2$/M phases and 90% in $G_0$/$G_1$ phases (FIG. 3A). Expression of Ki67 (FIG. 3B), a nuclear protein expressed during the S and $G_2$/M phases, and BrdU incorporation (FIG. 3B), which occurs in the S phase of the cell cycle, were both significantly higher in proliferating (SMGM) PASMC. TRPC6 protein expression also was enhanced in proliferating PASMC (FIG. 3B).

To examine if TRPC6 expression correlates with PASMC proliferation, the distribution of TRPC6 with Ki67 distribution was compared and BrdU incorporation in growth-arrested (SMBM) and proliferating (SMFM) PASMC. Only 6% of the growth-arrested cells were stained with both Ki67 and TRPC6, compared to 47% of the proliferating PASMC (FIG. 4A). Furthermore, a majority of S-phase cells (double-labeled by BrdU and Ki67) also expressed TRPC6 (FIG. 4B), indicating that its expression is elevated during DNA synthesis. Immunocytochemistry experiments also showed a link between TRPC6 and Ki67 expression. The Ki67-positive cells had higher level of TRPC6 than the Ki67-negative cells (FIG. 4C). These results indicate that the protein expression of TRPC6 in normal PASMC positively correlates with the incorporation and expression of markers of DNA synthesis and mitosis. The data also directed us to reason that TRPC6 expression is important for the transition from quiescence to DNA synthesis in proliferating PASMC.

To test whether upregulation of TRPC6 is involved in PASMC hyperplasia in IPAH patients, mRNA and protein levels of TRPC6 were compared in lung tissues and PASMC from NPH, IPAH, and SPH patients (Table 3). In lung tissues from IPAH patients, the protein level of TRPC6 was significantly higher than in NPH and SPH tissues (FIG. 5A). Because the vasculature forms a significant portion of the explanted lung tissues used experimentally, the high protein level of TRPC6 may be due to upregulated TRPC6 expression in PASMC. Indeed, the mRNA (FIG. 5B) and protein (FIG. 5C) levels of TRPC6 in IPAH-PASMC were much than in NPH- and SPH PASMC. Immunocytochemistry experiments confirmed that TRPC6 expression was significantly enhanced in IPAH-PASMC (FIG. 5D).

and C). This suggested that upregulated TRPC6 and 3 may increase the numbers of homo- and hetero-tetrameric channels which can be activated by mitogens and/or store depletion in IPAH-PASMC.

[$^3$H]-Thymidine incorporation (FIG. 7A) and BrdU uptake (FIG. 7B) were much greater in proliferating (SMGM) IPAH-PASMC than in SPH-PASMC, but comparable in growth-arrested (SMBM) cells. This indicated that the proliferative response to serum and growth factors was significantly enhanced in IPAH-PASMC. It suggested that if upregulated TRPC expression was responsible for IPAH-PASMC overgrowth, inhibition of TRPC expression would attenuate proliferation.

Transfection of TRPC6 siRNA into IPAH-PASMC significantly decreased TRPC6 protein expression (FIG. 8A) and [$^3$H]-thymidine incorporation in proliferating IPAH-PASMC (FIG. 8B, right panel); both were unaffected in IPAH-PASMC transfected with a scrambled oligonucleotide (Scram). [$^3$H]-thymidine incorporation into untreated cells was similar to that of Scram-treated cells (FIG. 8B, left panel). These results suggested that upregulated TRPC6 plays an important role in the overgrowth of IPAH-PASMC, and inhibition of TRPC6 can attenuate PASMC hyperplasia in IPAH patients.

The protein expression of TRPC6 in normal PASMC closely correlated with the expression of Ki67, suggesting that TRPC6 expression is involved in the transition of PASMC from quiescence to mitosis. In lung tissues and IPAH-PASMC, the mRNA and protein expression of TRPC3 and 6 were much higher than in those from normotensive or secondary pulmonary hypertension patients. Inhibition of TRPC6 expression with TRPC6-siRNA markedly attenuated

TABLE 3

Demographic and hemodynamic data of the patients

| Age | Sex/Race | Diagnosis | mPAP (mmHg) | PAOP (mmHg) | CO (l/min) | PVR* (mmHg·l$^{-1}$·min$^{-1}$) |
|---|---|---|---|---|---|---|
| 57 | F/AA | IPAH | 50 | 14 | 4.2 | 8.6 |
| 57 | F/C | IPAH | 66 | 7 | 4.9 | 12.0 |
| 32 | M/C | IPAH | 53 | 11 | 2.9 | 14.5 |
| 49.8 | | | 56.3 ± 4.9 | 10.7 ± 2.0 | 4.0 ± 0.6 | 11.7 ± 1.7 |
| 62 | F/C | CTEPH | 33 | 8 | 3.5 | 7.1 |
| 45 | F/C | CTEPH | 43 | 4 | 6.1 | 6.4 |
| 62 | F/C | CTEPH | 36 | 7 | 3.5 | 8.3 |
| 44 | F/C | CTEPH | 44 | 8 | 3.9 | 9.2 |
| 56 | M/C | COPD | 43 | NA | 4.6 | — |
| 60 | M/C | COPD | 33 | 15 | NA | NA |
| 69 | M/C | IPF | 26 | NA | 6.5 | — |
| 34 | F/C | LAM | 37 | 14 | 5.5 | 4.2 |
| 54.4 | | | 36.9 ± 2.2 | 9.3 ± 1.7 | 4.8 ± 0.5 | 7.0 ± 0.9 |
| 48 | M/C | COPD | 23 | 18 | 4.6 | 1.1 |
| 52 | F/C | COPD | 25 | 16 | NA | NA |
| 56 | F/AA | COPD | 16 | 6 | 3.6 | 2.8 |
| 52 ± 2 | | | 21.3 ± 2.7 | 13.3 ± 3.7 | 4.1 ± 0.5 | 1.9 ± 0.8 | mPAP, mean pulmonary arterial pressure; PAOP, pulmonary arterial occlusion pressure (wedge pressure); CO, cardiac output; F, female; M, male; AA, African American; C, Caucasian; IPAH, idiopathic pulmonary arterial hypertension; CTEPH, chronic thromboembolic pulmonary hypertension; IPF, idiopathic pulmonary fibrosis; LAM, lymphangioleiomyomatosis; COPD, chronic obstructive pulmonary disease; NA, data not available (not measured or cannot be estimated) for these patients.
*Calculated PVR based on the measured mPAP, PAOP, and CO.

TRPC6 shares significant homology with TRPC3. Hofmann et al. (1999) Nature 397: 259-263; Hofmann et al. (2002) Proc. Natl. Acad. Sci. 99: 7461-7466. Furthermore, TRPC3 can form homomeric channels, or can combine with TRPC6 to form heterotetrameric channels activated by second messengers and store depletion. TRPC3 was minimally expressed in NPH-PASMC (FIG. 2B; S); TRPC3 mRNA and protein expressions were considerably enhanced in PASMC from IPAH patients compared to SPH-PASMC (FIGS. 6A, B, IPAH-PASMC proliferation. These results demonstrate that expression of TRPC channels correlates with the progression of the cell cycle in PASMC. TRPC channel overexpression may be partially responsible for the increased PASMC proliferation and vascular medial hypertrophy in IPAH patients.

Sequencing

Methods for sequencing nucleic acids are well known in the art and may be used to practice any of the related embodiments. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Sequence preparation can be automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms that are well known in the art and described in Ausubel et al. (1997; Short Protocols in Molecular Biology, John Wiley & Sons, New York N.Y., unit 7.7) and Meyers (1995; Molecular Biology and Biotechnology, Wiley VCH, New York N.Y., pp. 856-853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the nucleic acid molecules of interest. Incomplete assembled sequences are inspected for identity using various algorithms or programs such as CONSED (Gordon (1998) Genome Res. 8: 195-202) that are well known in the art. Contaminating sequences including vector or chimeric sequences or deleted sequences can be removed or restored, respectively, organizing the incomplete assembled sequences into finished sequences.

Extension of a Polynucleotide Sequence

Polynucleotide sequences may be extended using PCR-based methods known in the art. For example, the XL-PCR kit (PE Biosystems), nested primers, and commercially available cDNA or genomic DNA libraries may be used to extend the polynucleotide sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, genomic DNA can be used rather than cDNA libraries.

Hybridization

The mammalian nucleic acid molecule and fragments thereof can be used in hybridization technologies for various purposes. A probe may be designed or derived from unique regions such as the 5' regulatory region or from a conserved motif such as the imidazoline receptor signature and used in protocols to identify naturally occurring molecules encoding the mammalian protein, allelic variants, or related molecules. The probe may be DNA or RNA, is usually single stranded and should have at least 50% sequence identity to any of the nucleic acid sequences. Hybridization probes may be produced using oligolabeling, nick translation, end-labeling, or PCR amplification in the presence of labeled nucleotide. A vector containing the nucleic acid molecule or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid molecules are completely complementary. In some membrane-based hybridizations, which can include 35%, and in other aspects 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. ((1989) Molecular Cloning. A Laboratory Manual, Cold Spring Harbor Press, Plainview N.Y.).

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and SNPs. Such information may be used to determine gene function; to understand the genetic basis of a condition, disease, or disorder; to diagnose a condition, disease, or disorder; and to develop and monitor the activities of therapeutic agents.

Hybridization probes are also useful in mapping the naturally occurring genomic sequence. The probes may be hybridized to: (a) a particular chromosome, (b) a specific region of a chromosome, or (c) artificial chromosome construction such as human artificial chromosome (HAC), yeast artificial chromosome (YAC), bacterial artificial chromosome (BAC), bacterial P1 construction, or single chromosome cDNA libraries.

Expression

A multitude of nucleic acid molecules encoding a SNP provided herein may be cloned into a vector and used to express the protein, or portions thereof, in host cells. The nucleic acid sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources that have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook.

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems. For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

Labeling of Molecules for Assay

A wide variety of labels and conjugation techniques are known by those skilled in the art and may be used in various nucleic acid, amino acid, and Ab assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The nucleic acid molecules, fragments, oligonucleotides, complementary RNA and DNA molecules, and PNAs may be used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia Vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

In one embodiment, the polynucleotide or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level which is observed in a normal subject. The results obtained from successive assays may be used to show the efficacy of treatment over a period ranging from several days to months.

Signal Detection/Quantitation Systems

The complexes formed by the assays disclosed herein can be detected, or detected and quantitated by any known detection/quantitation systems used in immunoassays. Abs can be used as tracers may be labeled in any manner directly or indirectly, that results in a signal that is visible or can be rendered visible.

Detectable marker substances include radionuclides, such as $^3$H, $^{125}$I, and $^{131}$I; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, $\alpha$-, $\beta$-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatase and paranitrophenyl phosphate (pNPP).

Detection, or detection and quantitation systems according to certain embodiments can produce luminescent signals, bioluminescent (BL) or chemiluminescent (CL). In CL or BL assays, the intensity or the total light emission is measured and related to the concentration of the analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, Vargulla and Renilla. Luminol can be used optionally with an enhancer molecule, which can be selected from the group consisting of 4-iodophenol or 4-hydroxycinnamic acid. Acridinium esters can be used. A signal is generated by treatment with an oxidant under basic conditions.

Luminescent detection systems can be used, wherein the signal is produced by an enzymatic reaction upon a substrate. CL and BL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g., AMPPD or CSPD; (Kricka, L. J., "Chemiluminescence and Bioluminescence, Analysis by," at p. 167, Molecular Biology and Biotechnology: A Comprehensive Desk Reference, ed. R. A. Meyers, VCH Publishers; N.Y., N.Y.; 1995)); a disodium salt of 4-methoxy-4-(3-phosphatephenyl)spiro [1,2-dioxetane-3,2'-adamantane] can be used, with or without an enhancer molecule, and 1-(trioctylphosphonium methyl)-4-(tributylphosphonium methyl) benzene diochloride. HRP is preferably used with substrates, such as, 2', 3', 6'-trifluorophenyl 3-methoxy-10-methylacridan-9-carboxylate.

CL and BL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases; and dehydrogenases, and can be used to measure any component of the coupled reaction (enzyme, substrate, cofactor).

In certain aspects, the detectable marker may be directly or indirectly linked to an Ab used. Exemplary of an indirect linkage of the detectable label is the use of a binding pair between the Ab and the marker, or the use of well known signal amplification signals, such as, using a biotinylated Ab complexed to UGP and then adding streptavidin conjugated to HRP and then TMB.

Exemplary of binding pairs that can be used to link Abs to detectable markers are biotin/avidin, streptavidin, or anti-biotin; avidin/anti-avidin; thyroxine/thyroxine-binding globulin; antigen/Ab; Ab/anti-Ab; carbohydrate/lectins; hapten/anti-hapten Ab; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins. Binding pairs can be biotin/avidin or streptavidin, and biotin/streptavidin.

Various means for linking labels directly or indirectly to Abs are known in the art. For example, labels may be bound either covalently or non-covalently. Exemplary Ab conjugation methods are described in: Avarmeas, et al., Scan. J. Immunol., 8 (Suppl. 7):7 (1978); Bayer, et al., Meth. Enzymol., 62:308 (1979); Chandler, et al., J. Immunol. Meth., 53:187 (1982); Ekeke and Abuknesha, J. Steroid Biochem., 11:1579 (1979); Engvall and Perlmann, J. Immunol., 109:129 (1972); Geoghegan, et al., Immunol. Comm., 7:1 (1978); and Wilson and Nakane, Immunofluorescence and Related Techniques, p. 215 (Elsevier/North Holland Biomedical Press; Amsterdam (1978)).

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

Screening Assays

The nucleic acid molecule encoding the mammalian SNP may be used to screen a library of molecules or compounds for specific binding affinity. The libraries may be DNA molecules, RNA molecules, PNAs, peptides, proteins such as transcription factors, enhancers, repressors, and other ligands that regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule which specifically binds the nucleic acid molecule.

Similarly the mammalian protein or a portion thereof may be used to screen libraries of molecules or compounds. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, Abs, immunoglobulins, inhibitors, peptides, proteins, drugs, or any other ligand, which specifically binds the protein. One method for high throughput screening described in U.S. Pat. No. 5,876,946, is incorporated herein by reference, and discloses methods for screening large numbers of molecules for enzyme inhibition or receptor binding.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations. Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle that produces the number of organisms needed to satisfy statistical requirements.

Acute toxicity tests are based on a single administration of the agent to the subject to determine the symptomology or lethality of the agent. Three experiments are conducted: (a) an initial dose-range-finding experiment, (b) an experiment to narrow the range of effective doses, and (c) a final experiment for establishing the dose-response curve.

Prolonged toxicity tests are based on the repeated administration of the agent. Rats and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Animal Models

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Transgenic rodents which over-express or under-express a gene of interest may be inbred and used to model human diseases or to test therapeutic or toxic agents. In some cases, the introduced gene may be activated at a specific time in a specific tissue type during fetal development or postnatally. Expression of the transgene is monitored by analysis of phenotype or tissue-specific mRNA expression in transgenic animals before, during, and after challenge with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells can be used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene that disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Transformed ES cells are identified, and can be microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes. Recent developments demonstrate that ES cells derived from human blastocysts may also be manipulated in vitro to differentiate into eight separate cell lineages, including endoderm, mesoderm, and ectodermnal cell types. Thomson (1998) Science 282: 1145-1147.

Knockout Analysis

In gene knockout analysis, a region of a human disease gene candidate is enzymatically modified to include a non-mammalian gene such as the neomycin phosphotransferase gene (see, for example, Capecchi (1989) Science 244: 1288-1292). The inserted coding sequence disrupts transcription and translation of the targeted gene and prevents biochemical synthesis of the disease candidate protein. The modified gene is transformed into cultured embryonic stem cells, the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells that contain the integrated human gene are handled as described above. Inbred animals are studied and treated to obtain information on the analogous human condition. These methods have been used to model several human diseases. Lee et al. (1998) Proc. Natl. Acad. Sci. 95: 11371-11376; Baudoin et al. (1998) Genes Dev. 12: 1202-1216; and Zhuang et al. (1998) Mol. Cell Biol. 18: 3340-3349.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulata*) and common marmosets (*Callithrix jacchus*) are the most common non-human primates (NHPs)

used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as "extensive metabolizers" and "poor metabolizers" of these agents.

In additional embodiments, the polynucleotides which encode the mammalian SNP may be used in any molecular biology techniques that have yet to be developed, provided the new techniques rely on properties of nucleic acid molecules that are currently known, including, but not limited to, such properties as the triplet genetic code and specific base pair interactions.

The in vitro experiments have shown that treatment of PASMC from patients with IPAH with the TRPC6 siRNA (SEQ ID NO: 5) significantly inhibits the mRNA and protein expression levels of TRPC6. A polynucleotide expression vector comprising SEQ ID NO: 5 can be injected into the pulmonary vasculature of an experimental rat via a pulmonary arterial catheter to demonstrate that the expression of SEQ ID NO: 5 as a ribonucleic acid (siRNA) in vivo can downregulate TRPC6 expression in either cultured PASMC or the pulmonary arteries in vivo. The levels of expression of TRPC6 can be determined by Western blot analysis and immunohistological method. Such methods are well known in the art. See, for example, U.S. Pat. No. 6,673,917, herein incorporated by reference in its entirety.

In addition, analysis of an animal model of IPAH can be performed using SEQ ID NO: 5 to determine how siRNA-mediated downregulation of TRPC6 channel expression can attenuate hypoxia-mediated pulmonary hypertension. Chronic exposure to hypoxia (10% oxygen) for a week causes pulmonary hypertension in rats. The pulmonary arterial pressure (PAP) can be measured by a catheter placed in the main pulmonary artery via the jugular vein. PAP can be compared between the rats treated (or injected) with the vector comprising a variant of SEQ ID NO: 5, or SEQ ID NO: 6 that can express TRPC6 siRNA and control rats injected with a scrambled siRNA vector (which serves as a nonsilencing control). After measurement of PAP, lung tissue, pulmonary arteries, and PASMC can be removed and isolated from the animals. The tissue can be sampled to detect mRNA and protein expression level of TRPC6.

Anti-TRPC6 and SNP Abs

The invention makes use of Abs and antibody fragments, such as $F_{ab}$ or $(F_{ab})_2$, that bind immunospecifically to any TRPC6 epitope or. "Antibody" (Ab) comprises single Abs directed against TRPC6 protein (anti-TRPC6 Ab; including agonist, antagonist, and neutralizing Abs), anti-TRPC6 Ab compositions with poly-epitope specificity, single chain anti-TRPC6 Abs, and fragments of anti-TRPC6 Abs. A "monoclonal antibody" is obtained from a population of substantially homogeneous Abs, i.e., the individual Abs comprising the population are identical except for possible naturally-occurring mutations that may be present in minor amounts. Exemplary Abs include polyclonal (pAb), monoclonal (mAb), humanized, bi-specific (bsAb), and heteroconjugate Abs. Abs can be produced by any known method in the art or obtained commercially.

Monovalent Abs

The Abs may be monovalent Abs that consequently do not cross-link with each other. For example, one method involves recombinant expression of Ig light chain and modified heavy chain. Heavy chain truncations generally at any point in the $F_c$ region will prevent heavy chain cross-linking. Alternatively, the relevant cysteine residues are substituted with another amino acid residue or are deleted, preventing crosslinking. In vitro methods are also suitable for preparing monovalent Abs. Abs can be digested to produce fragments, such as $F_{ab}$ fragments.

Humanized and Human Abs

Anti-TRPC6 Abs may further comprise humanized or human Abs. Humanized forms of non-human Abs are chimeric Igs, Ig chains or fragments (such as $F_v$, $F_{ab}$, $F_{ab'}$, $F_{(ab')2}$ or other antigen-binding subsequences of Abs) that contain minimal sequence derived from non-human Ig.

Generally, a humanized Ab has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human. Ab. Such "humanized" Abs are chimeric Abs, wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient Ab) in which residues from a complementary determining region (CDR) of the recipient are replaced by residues from a CDR of a non-human species (donor Ab) such as mouse, rat or rabbit, having the desired specificity, affinity and capacity. In some instances, corresponding non-human residues replace $F_v$ framework residues of the human Ig. Humanized Abs may comprise residues that are found neither in the recipient Ab nor in the imported CDR or framework sequences. In general, the humanized Ab comprises substantially all of at least one, and typically two, variable domains, in which most if not all of the CDR regions correspond to those of a non-human Ig and most if not all of the FR regions are those of a human Ig consensus sequence. The humanized Ab optimally also comprises at least a portion of an Ig constant region ($F_c$), typically that of a human Ig.

Human Abs can also be produced using various techniques, including phage display libraries and the preparation of human mAbs. Similarly, introducing human Ig genes into transgenic animals in which the endogenous Ig genes have been partially or completely inactivated can be exploited to synthesize human Abs. Upon challenge, human Ab production is observed, which closely resembles that seen in humans in all respects, including gene rearrangement, assembly, and Ab repertoire.

Bi-specific mAbs

Bi-specific Abs are monoclonal, preferably human or humanized, that have binding specificities for at least two different antigens. For example, a binding specificity is TRPC6; the other is for any antigen of choice, preferably a cell-surface protein or receptor or receptor subunit. Traditionally, the recombinant production of bi-specific Abs is based on the co-expression of two Ig heavy-chain/light-chain pairs, where the two heavy chains have different specificities. Because of the random assortment of Ig heavy and light chains, the resulting hybridomas (quadromas) produce a potential mixture of ten different Ab molecules, of which only one has the desired bi-specific structure. The desired Ab can be purified using affinity chromatography or other techniques.

To manufacture a bi-specific Ab, variable domains with the desired Ab-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of Ab molecules can be engineered to maximize the percentage of heterodimers that are recovered from recombinant cell culture. The preferred interface comprises at least part of the CH3 region of an Ab constant domain. In this method, one or more small amino acid side chains from the interface of the first Ab molecule are replaced with larger side chains (e.g., tyrosine or tryptophan). Compensatory "cavities" of identical or similar size to the large side chain(s) are created on the interface of the second Ab molecule by replacing large amino acid side chains with smaller ones (e.g., alanine or threonine). This mechanism increases the yield of the heterodimer over unwanted end products such as homodimers.

Bi-specific Abs can be prepared as full length Abs or Ab fragments (e.g., $F_{(ab')2}$ bi-specific Abs). One technique to generate bi-specific Abs exploits chemical linkage. Intact Abs can be proteolytically cleaved to generate $F_{(ab')2}$ fragments. Fragments are reduced with a dithiol complexing agent, such as sodium arsenite, to stabilize vicinal dithiols and prevent intermolecular disulfide formation. The generated $F_{ab'}$ fragments are then converted to thionitrobenzoate (TNB) derivatives. One of the $F_{ab'}$-TNB derivatives is then reconverted to the $F_{ab'}$-thiol by reduction with mercaptoethylamine and is mixed with an equimolar amount of the other $F_{ab'}$-TNB derivative to form the bi-specific Ab. The produced bi-specific Abs can be used as agents for the selective immobilization of enzymes.

$F_{ab'}$ fragments may be directly recovered from E. coli and chemically coupled to form bi-specific Abs. For example, fully humanized bi-specific $F_{(ab')2}$ Abs can be produced by methods known to those of skill in the art. Each $F_{ab'}$ fragment is separately secreted from E. Coli and directly coupled chemically in vitro, forming the bi-specific Ab.

Various techniques for making and isolating bi-specific Ab fragments directly from recombinant cell culture have also been described. For example, leucine zipper motifs can be exploited. Peptides from the Fos and Jun proteins are linked to the $F_{ab'}$ portions of two different Abs by gene fusion. The Ab homodimers are reduced at the hinge region to form monomers and then re-oxidized to form Ab heterodimers. This method can also produce Ab homodimers. The "diabody" technology provides an alternative method to generate bi-specific Ab fragments. The fragments comprise a heavy-chain variable domain ($V_H$) connected to a light-chain variable domain ($V_L$) by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific Ab fragments is the use of single-chain $F_v$ ($sF_v$) dimers. Abs with more than two valences are also contemplated, such as tri-specific Abs.

Exemplary bi-specific Abs may bind to two different epitopes on a given TRPC6. Alternatively, cellular defense mechanisms can be restricted to a particular cell expressing the particular TRPC6: an anti-TRPC6 arm may be combined with an arm that binds to a leukocyte triggering molecule, such as a T-cell receptor molecule (e.g., CD2, CD3, CD28, or B7), or to $F_c$ receptors for IgG ($F_c\gamma R$), such as $F_c\gamma RI$ (CD64), $F_c\gamma RII$ (CD32) and $F_c\gamma RIII$ (CD16). Bi-specific Abs may also be used to target cytotoxic agents to cells that express a particular TRPC6. These Abs possess a TRPC6-binding arm and an arm that binds a cytotoxic agent or a radionuclide chelator.

Heteroconjugate Abs

Heteroconjugate Abs, consisting of two covalently joined Abs, have been proposed to target immune system cells to unwanted cells and for treatment of human immunodeficiency virus (HIV) infection. Abs prepared in vitro using synthetic protein chemistry methods, including those involving cross-linking agents, are contemplated. For example, immunotoxins may be constructed using a disulfide exchange reaction or by forming a thioether bond. Examples of suitable reagents include iminothiolate and methyl-4-mercaptobutyrimidate.

Diagnostic Applications of Abs Directed Against TRPC6

Anti-TRPC6 Abs can be used to localize and/or quantitate TRPC6 (e.g., for use in measuring levels of TRPC6 within tissue samples or for use in diagnostic methods, etc.). Anti-TRPC6 epitope Abs can be utilized as pharmacologically active compounds and screened according to the methods of the present invention.

Anti-TRPC6 Abs can be used to isolate TRPC6 by standard techniques, such as immunoaffinity chromatography or immunoprecipitation. These approaches facilitate purifying endogenous TRPC6 antigen-containing polypeptides from cells and tissues. These approaches, as well as others, can be used to detect TRPC6 in a sample to evaluate the abundance and pattern of expression of the antigenic protein. Anti-TRPC6 Abs can be used to monitor protein levels in tissues as part of a clinical testing procedure; for example, to determine the efficacy of a given treatment regimen. Coupling the Ab to a detectable substance (label) allows detection of Ab-antigen complexes. Classes of labels include fluorescent, luminescent, bioluminescent, and radioactive materials, enzymes and prosthetic groups. Useful labels include horseradish peroxidase, alkaline phosphatase, β-galactosidase, acetylcholinesterase, streptavidin/biotin, avidin/biotin, umbelliferone, fluorescein, fluorescein isothiocyanate, rhodamine, dichlorotriazinylamine fluorescein, dansyl chloride, phycoerythrin, luminol, luciferase, luciferin, aequorin, and $^{125}I$, $^{131}I$, $^{35}S$ or $^3H$.

Ab Therapeutics

Abs of the invention, including polyclonal, monoclonal, humanized and fully human Abs, can be used therapeutically. Such agents will generally be employed to treat or prevent a disease or pathology in a subject. An Ab preparation, preferably one having high antigen specificity and affinity generally mediates an effect by binding the target epitope(s). Generally, administration of such Abs may mediate one of two effects: (1) the Ab may prevent ligand binding, eliminating endogenous ligand binding and subsequent signal transduction, or (2) the Ab elicits a physiological result by binding an effector site on the target molecule, initiating signal transduction.

A therapeutically effective amount of an Ab relates generally to the amount needed to achieve a therapeutic objective, epitope binding affinity, administration rate, and depletion rate of the Ab from a subject. Common ranges for therapeutically effective doses may be, as a nonlimiting example, from about 0.1 mg/kg body weight to about 50 mg/kg body weight. Dosing frequencies may range, for example, from twice daily to once a week.

Pharmaceutical Compositions for Abs

Anti-TRPC6 Abs, as well as other TRPC6 interacting molecules (such as aptamers) identified in other assays, can be administered in pharmaceutical compositions as disclosed, infra, to treat various disorders. Abs that are internalized are preferred when whole Abs are used as inhibitors. Liposomes may also be used as a delivery vehicle for intracellular introduction. Where Ab fragments are used, the smallest inhibitory fragment that specifically binds to the epitope is preferred. For example, peptide molecules can be designed that bind a preferred epitope based on the variable-region sequences of a useful Ab. Such peptides can be synthesized chemically and/or produced by recombinant DNA technology. Formulations may also contain more than one active compound for a particular treatment, preferably those with activities that do not adversely affect each other. The composition may comprise an agent that enhances functions such as a cytotoxic agent, cytokine; chemotherapeutic agent, or growth-inhibitory agent.

The active ingredients can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions. The formulations to be used for in vivo administration are highly preferred to be sterile. This is readily accomplished by filtration through sterile filtration membranes or any of a number of techniques.

Sustained-release preparations may also be prepared, such as semi-permeable matrices of solid hydrophobic polymers containing the Ab, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as injectable microspheres composed of lactic acid-glycolic acid copolymer, and poly-D-(−)-3-hydroxybutyric acid. While polymers such as ethylene-vinyl acetate and lactic acid-glycolic acid enable release of molecules for over 100 days, certain hydrogels release proteins for shorter time periods and may be preferred.

Pharmaceutical Preparations and Methods of Administration

The identified compounds treat, inhibit, control and/or prevent, or at least partially arrest or partially prevent pulmonary arterial hypertension, and can be administered to a subject at therapeutically effective doses for the inhibition, prevention, prophylaxis or therapy for such a disorder. The compounds can comprise a therapeutically effective dosage of a polypeptide, a term which includes therapeutically, inhibitory, preventive and prophylactically effective doses of the compounds of the present invention and is more particularly defined below. Without being bound to any particular theory, applicants surmise that these pharmaceutical compounds prevent activity of a transient receptor potential cation channel when administered to a subject suffering from a related condition by inhibiting activity of NF-κB. The subject can be an animal, including, but not limited to, mammals, reptiles and avians, also including horses, cows, dogs, cats, sheep, pigs, and chickens, and can be human.

Therapeutically Effective Dosage

Toxicity and therapeutic efficacy of such compounds can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$.

Compounds that exhibit large therapeutic indices are preferred. While compounds exhibiting toxic side effects may be used, care should be taken to design a delivery system that targets such compounds to the site affected by the disease or disorder in order to minimize potential damage to unaffected cells and reduce side effects.

The data obtained from the cell culture assays and animal studies can be used in formulating a range of dosages for use in humans and other mammals. The dosage of such compounds lies preferably within a range of circulating plasma or other bodily fluid concentrations that include the $ED_{50}$ with little or no toxicity. The dosage may vary within this range depending upon the dosage form employed and the route of administration utilized. For any compound of the invention, the therapeutically effective dose can be estimated initially from cell culture assays. A dosage may be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful dosages in humans and other mammals. Compound levels in plasma may be measured, for example, by high performance liquid chromatography.

The amount of a compound that may be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a disease or condition with the compounds of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a compound delivery system is utilized and whether the compound is administered as a pro-drug or part of a drug combination. Thus, the dosage regime actually employed may vary widely from subject to subject.

Formulations and Use

The compounds of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by ionic, covalent, Van der Waals, hydrophobic, hydrophillic or other physical forces. It is preferred that administration is localized in a subject, but administration may also be systemic.

The compounds of the present invention may be formulated by any conventional manner using one or more pharmaceutically acceptable carriers and/or excipients. Thus, the compounds and their pharmaceutically acceptable salts and solvates may be specifically formulated for administration, e.g., by inhalation or insufflation (either through the mouth or the nose) or oral, buccal, parenteral or rectal administration. The compounds may take the form of charged, neutral and/or other pharmaceutically acceptable salt forms. Examples of pharmaceutically acceptable carriers include, but are not limited to, those described in Remington's Pharmaceutical Sciences (A. R. Gennaro, Ed.), 21st edition, ISBN: 0781746736 (2005), incorporated herein by reference in its entirety.

The compounds may also take the form of solutions, suspensions, emulsions, tablets, pills, capsules, powders, controlled- or sustained-release formulations and the like. Such formulations will contain a therapeutically effective amount of the compound, preferably in purified form, together with a suitable amount of carrier so as to provide the form for proper administration to the patient. The formulation should suit the mode of administration.

Parenteral Administration

The compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compound may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 5 percent to about 20 percent, more preferably from about 5 percent to about 17 percent, more preferably from about 8 to about 14 percent, and still more preferably about 10 percent of the compound. The solution or powder preparation may also include a solubilizing agent and a local anesthetic such as lignocaine to ease pain at the site of the injection. Other methods of parenteral delivery of compounds will be known to the skilled artisan and are within the scope of the invention.

Oral Administration

For oral administration, the compound may take the form of tablets or capsules prepared by conventional means with pharmaceutically acceptable excipients such as binding agents, fillers, lubricants and disintegrants:

A. Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101 AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

B. Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

C. Lubricants

Lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W. R. Grace Co. of Baltimore, Md., USA), a coagulated aerosol of synthetic silica (marketed by Deaussa Co. of Piano, Tex., USA), CAB-O-SIL (a pyrogenic silicon dioxide product sold by Cabot Co. of Boston, Mass., USA), and mixtures thereof.

D. Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

The tablets or capsules may optionally be coated by methods well known in the art. If binders and/or fillers are used with the compounds of the invention, they are typically formulated as about 50 to about 99 weight percent of the compound. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall, Solid Oral Dosage Forms, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound.

In addition, the compounds of the present invention may be formulated for buccal administration in the form of tablets or lozenges formulated in a conventional manner. Other methods of oral delivery of compounds will be known to the skilled artisan and are within the scope of the invention.

Controlled-Release Administration

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a compound that produces the desired therapeutic effect, and gradually and continually release other amounts of the compound to maintain the level of therapeutic effect over an extended period of time. In order to maintain a near-constant level of a compound in the body, the compound can be released from the dosage form at a rate that will replace the amount of compound being metabolized and/or excreted from the body. The controlled-release of a compound may be stimulated by various inducers, e.g., change in pH, change in temperature, enzymes, water, or other physiological conditions or molecules.

Controlled-release systems may include, for example, an infusion pump which may be used to administer the compound in a manner similar to that used for delivering insulin or chemotherapy to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The compounds of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

Inhalation Administration

The compound may also be administered directly to the lung by inhalation. For administration by inhalation, a compound may be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas may be used to deliver a compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer a compound to the lung. DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver a compound to the lung is a liquid spray device supplied, for example, by Aradigm Corporation. Liquid spray systems use extremely small nozzle holes to aerosolize liquid compound formulations that may then be directly inhaled into the lung. For example, a nebulizer device may be used to deliver a compound to the lung. Nebulizers create aerosols from liquid compound formulations by using, for example, ultrasonic energy to form fine particles that may be readily inhaled. Examples of nebulizers include devices supplied by Sheffield/Systemic Pulmonary Delivery Ltd., Aventis and Batelle Pulmonary Therapeutics.

In another example, an electrohydrodynamic ("EHD") aerosol device may be used to deliver a compound to the lung. EHD aerosol devices use electrical energy to aerosolize liquid compound solutions or suspensions. The electrochemical properties of the compound formulation are important parameters to optimize when delivering this compound to the lung with an EHD aerosol device. Such optimization is routinely performed by one of skill in the art. Other methods of intrapulmonary delivery of compounds will be known to the skilled artisan and are within the scope of the invention.

Liquid compound formulations suitable for use with nebulizers and liquid spray devices and EHD aerosol devices will typically include the compound with a pharmaceutically acceptable carrier. In one exemplary embodiment, the pharmaceutically acceptable carrier is a liquid such as alcohol, water, polyethylene glycol or a perfluorocarbon. Optionally, another material may be added to alter the aerosol properties of the solution or suspension of the compound. For example, this material may be a liquid such as an alcohol, glycol, polyglycol or a fatty acid. Other methods of formulating liquid compound solutions or suspensions suitable for use in aerosol devices are known to those of skill in the art.

Depot Administration

The compound may also be formulated as a depot preparation. Such long-acting formulations may be administered by implantation (e.g., subcutaneously or intramuscularly) or by intramuscular injection. Accordingly, the compounds may be formulated with suitable polymeric or hydrophobic materials such as an emulsion in an acceptable oil or ion exchange resins, or as sparingly soluble derivatives such as a sparingly soluble salt. Other methods of depot delivery of compounds will be known to the skilled artisan and are within the scope of the invention.

Topical Administration

For topical application, the compound may be combined with a carrier so that an effective dosage is delivered, based on the desired activity ranging from an effective dosage, for example, of 1.0 µM to 1.0 mM. In one aspect of the invention, a topical compound can be applied to the skin. The carrier may be in the form of, for example, and not by way of limitation, an ointment, cream, gel, paste, foam, aerosol, suppository, pad or gelled stick.

A topical formulation may also consist of a therapeutically effective amount of the compound in an opthalmologically acceptable excipient such as buffered saline, mineral oil, vegetable oils such as corn or arachis oil, petroleum jelly, Miglyol 182, alcohol solutions, or liposomes or liposome-like products. Any of these compounds may also include preservatives, antioxidants, antibiotics, immunosuppressants, and other biologically or pharmaceutically effective agents which do not exert a detrimental effect on the compound. Other methods of topical delivery of compounds will be known to the skilled artisan and are within the scope of the invention.

Suppository Administration

The compound may also be formulated in rectal formulations such as suppositories or retention enemas containing conventional suppository bases such as cocoa butter or other glycerides and binders and carriers such as triglycerides, microcrystalline cellulose, gum tragacanth or gelatin. Suppositories can contain the compound in the range of 0.5% to 10% by weight. Other methods of suppository delivery of compounds will be known to the skilled artisan and are within the scope of the invention.

Other Systems of Administration

Various other delivery systems are known in the art and can be used to administer the compounds of the invention. Moreover, these and other delivery systems may be combined and/or modified to optimize the administration of the compounds of the present invention. Exemplary formulations using the compounds of the present invention are described below (the compounds of the present invention are indicated as the active ingredient, but those of skill in the art will recognize that pro-drugs and compound combinations are also meant to be encompassed by this term):

Formulation 1

Hard gelatin capsules are prepared using the following ingredients:

TABLE 4

| Ingredients | (mg/capsule) |
|---|---|
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the following ingredients:

TABLE 5

| Ingredients | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

TABLE 6

| Ingredients | Weight % |
|---|---|
| Active ingredient | 5 |
| Lactose | 95 |

The active ingredient is mixed with the lactose and the mixture is added to a dry powder inhaling appliance.

Formulation 4

Tablets, each containing 60 mg of active ingredient, are prepared as follows:

TABLE 7

| Ingredients | milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of active ingredient are made as follows:

TABLE 8

| Ingredients | milligrams |
|---|---|
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient, are made as follows:

TABLE 9

| Ingredients | milligrams |
|---|---|
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE 10

| Ingredients | milligrams |
| --- | --- |
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xanthan gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of active ingredient, are made as follows:

TABLE 11

| Ingredients | milligrams |
| --- | --- |
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Kits

In various embodiments, the present invention can also involve kits. Such kits can include the compounds of the present invention and, in certain embodiments, instructions for administration. When supplied as a kit, different components of a compound formulation can be packaged in separate containers and admixed immediately before use. Such packaging of the components separately can, if desired, be presented in a pack or dispenser device which may contain one or more unit dosage forms containing the compound. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may also include reagents in separate containers such as, for example, sterile water or saline to be added to a lyophilized active component packaged separately. For example, sealed glass ampules may contain lyophilized polypeptides, and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit, or supplied as electronic mail.

The invention will be more readily understood by reference to the following examples, which are included merely for purposes of illustration of certain aspects and embodiments of the present invention and not as limitations.

EXAMPLES

Example 1

Association of a SNP in the TRPC6 Gene with IPAH

The possibility that SNPs in the putative TRPC6 promoter may underlie the upregulated TRPC6 protein expression in IPAH-PASMC was investigated.

72 normal subjects, 67 patients with secondary pulmonary hypertension (SPH), and 161 patients diagnosed with IPAH based on the criteria set forth by the National Institutes of Health Registry for Primary Pulmonary Hypertension participated in this study. Informed consent, approved by the University of California Institutional Review Board, was obtained from all patients. All SPH and IPAH patients underwent right-heart catherization as part of the standard diagnostic procedure for pulmonary hypertension.

Blood samples were collected from 72 normal subjects (mean PAP: 13±5 mmHg; which was only measured in some subjects), 67 SPH patients (mean PAP: 48±12 mmHg), and 161 IPAH patients (mean PAP: 54±14 mmHg). A flow-directed balloon-tipped Swan-Ganz catheter (Baxter Healthcare Corporation) was positioned into pulmonary artery via the internal jugular vein. Hemodynamic measurements (PAP) were obtained by a pressure transducer (Namic, Boston Scientific) connected to a Mac-Laboratory 7000 hemodynamic and electrocardiographic monitoring system (GE Medical System). The PAP signals were sampled at 200 Hz and stored on a computer for later analysis.

Blood samples (2-3 ml) were collected from patients via the pulmonary catheter and stored in EDTA-containing tubes at −80° C. until use. Genomic DNA was extracted from the blood samples using a DNA isolation kit according to the manufacturer's instruction (PUREGENE, Gentra Systems, Minneapolis Minn.). DNA purity was measured as the ratio of the absorbance at 260 and 280 nm (1 cm lightpath; $A_{260}/A_{280}$) measured with a Beckman spectrophotometer.

The promoter region of TRPC6 gene from each patient's DNA sample was amplified by PCR using the primers specifically designed for the region (see Table 2). The PCR products were sequenced by the Core Facility at UCSD. SNPs identified in the sequence traces were verified using Phred/Phrap/Consed software and compared with known SNPs deposited in the NCBI SNP databank.

Genomic DNA was sequenced using the polymerase chain reaction (PCR) and primers shown in Table 12. The primers were designed using the human TRPC6 nucleotide sequence (SEQ ID NO: 2).

Statistical Analysis: Values are expressed as mean ±SD. $X^2$ analysis was used (Web Chi Square Calculator, Georgetown Linguistics, Georgetown University, Washington D.C.) to assess differences between genotype frequencies in normal subjects, patients with SPH, and patients with IPAH. One-way ANOVA with post-hoc analysis was performed as indicated to compare hemodynamics between different patient groups.

TABLE 12

Sequences of the primers used for sequencing the TRPC6 gene promoter region

| Amplicon | Size (bp) | Sense/Antisense | Location (nt)* |
|---|---|---|---|
| 1 | 466 | 5'-TTCCCCATACTTGGTGTTGCC-3'/<br>5'-AGCAGAAACCACTTGTCCTG-3'<br>(SEQ ID NOs: 7 and 8, respectively) | 162-182<br>607-627 |
| 2 | 491 | 5'-CCTGTGTCAAATACGAAGCTGG-3'/<br>5'-GGAGGCAAAGAAGCAGATGAG-3'<br>(SEQ ID NOs: 9 and 10, respectively) | 580-601<br>1050-1070 |
| 3 | 426 | 5'-AATTGGTCCCCCTTTCTGCCAC-3'/<br>5'-AACGCCAGATGTTCCCAGTTCC-3<br>(SEQ ID NOs: 11 and 12, respectively) | 1001-1022<br>1405-1426 |
| 4 | 451 | 5'-TTGCATTCGCAGTGACGGAAGG-3'/<br>5'-AGAAAGCAGCCAAAGCCTGTCC-3<br>(SEQ ID NOs: 13 and 14, respectively) | 1297-1318<br>1726-1747 |
| 5 | 490 | 5'-AGAAAGAAGAGGCTCGTGTCC-3'/<br>5'-GAAAAGTCACCACTTAAGGGGG-3<br>(SEQ ID NOs: 15 and 16, respectively) | 1526-1546<br>1994-2015 |
| 6 | 439 | 5'-TTGCTCTCCGCTCTTACGCTTC-3'/<br>5'-TCCATGAGCAGATAGTCCTGGC-3'<br>(SEQ ID NOs: 17 and 18, respectively) | 1867-1888<br>2284-2305 |

*Location described in nucleotides 5' of the translational start site (ATG)

Isolation of SNPs

High fidelity amplification of genomic DNA of putative TRPC6 promoter region was performed by a GENEAMP PCR System (Perkin Elmer) using a PLATINUM PCR SUPERMIX kit (Invitrogen). The 50 µl PCR reaction mix contained the DNA template, consisting of 0.2 µM of each primer, 10 mM Tris-HCl, pH 8.3, 50 mM KCl, 2 mM $MgCl_2$, 200 µM each dNTP, and 2 U Taq DNA polymerase. The DNA samples were amplified in a DNA thermal cycler under the following conditions: Step 1: the mixture was denatured at 94° C. for 3 min; step 2: the sample was denatured at 94° C. (30 sec); step 3: sample annealed at 55° C. (30 sec); step 4: sample extended at 72° C. (30 sec). Steps 2, 3, and 4 were repeated for 35 cycles, followed by a final extension at 72° C. (10 min) to ensure complete product extension.

The PCR products were separated through a 1.5% agarose gel and amplified DNA bands were visualized by GELSTAR staining (Cambrex). Three biallelic SNPs were identified in the 2000-bp sequence upstream of the TRPC6 ATG site: A-361T, C-254G, and C-218T.

FIG. 1B shows the 425 nucleotides 5' of the ATG site (SEQ ID NO: 2) of the putative promoter region of the human TRPC6 gene as well as the initial 75 nucleotides of the coding sequence (NCBI; Accession No. NM_004621; GI:19923256).

Of the three biallelic SNPs, A-361T (variant SNP-2A and SNP2T, of SEQ ID NO: 2) was novel, C-254G (variant SNP-1C and SNP-1G of SEQ ID NO: 2) had been previously reported as SNP ID No. rs 3824934, and C-218T (variant SNP-3C and SNP-3T of SEQ ID NO: 2) was novel.

The A-361T SNP generated a putative His4 hotspot site (TGACT); the His4 hotspot binds several eukaryotic transcription factors (including GCN4 and/or RAP1 at the TGACT-region) and appears to be involved in recombination activation during meiosis in yeast.

The C-218T SNP of SEQ ID NO: 2 occurred in a putative palindrome motif sequence AAGATCCTCTT (SEQ ID NO: 27) that is similar in size and arrangement to nuclear receptors that form homo- or hetereodimers on their respective TRE(s).

The putative TREs are double underlined in FIG. 1B. The presence of the A-361T SNP was always (100% of cases) linked to occurrence of the C-218T SNP but it has not been identified as a known binding site for a transcription factor. In addition, the A-361T and C-218T SNPs are separated by a distance of 143 bp, a distance similar to that of the 146 bp of DNA comprising a mammalian nucleosome core. This suggested that the occurrence linkage. between the A-361T SNP and the C-218T sites and the respective putative TREs may have functional significance.

The allele frequency of the A-361T and C-218T SNPs was not significantly different between IPAH and normal subjects or SPH patients. However, the C-254G SNP had a significantly higher allele frequency in IPAH patients (0.137) (P<0.05) than in normal subjects (0.077) and SPH patients (0.0896) (FIG. 1D and Table 13). Furthermore, 9 out 161 (6%) IPAH patients were the homozygous GG genotype, whereas 3% of SPH patients and none of the normal subjects were the homozygous GG genotype (P<0.05) (Table 14). The C to G nucleotide change associated with the C-254G SNP generates a potential NF-κB binding site in the TRPC6 gene promoter (FIG. 1B).

TABLE 13

Allele frequencies of the SNPs identified in the promoter
region of TRPC6 gene in normal subjects and patients with
secondary pulmonary hypertension (SPH) or IPAH

| Position | SNP | Normal Subjects (n = 72) | SPH-Patients (n = 67) | IPAH Patients (n = 161) | P-values* |
|---|---|---|---|---|---|
| −361 | A T | 0.254 | 0.194 | 0.236 | 0.706 |
| −254 | C G | 0.077 | 0.0896 | 0.137 | 0.0365 |
| −218 | C T | 0.254 | 0.194 | 0.236 | 0.706 |

*P-values were calculated using $X^2$ analysis for comparison of the allele frequencies in IPAH patients with normal subjects and SPH patients.

TABLE 14

Genotype frequencies of the SNP (C-254G) in the TRPC6 gene
promoter in normal subjects and patients with SPH or IPAH.

| | Normal Subjects (n = 72) | SPH Patients (n = 67) | IPAH Patients (n = 161) | P-values** |
|---|---|---|---|---|
| Mean PAP (mmHg) (means ± SD) | 13.2 ± 4.9* | 47.7 ± 12.0 | 54.2 ± 13.9 | <0.001 |
| Genotype | | | | |
| CC | 60 (83.34%) | 55 (82.09%) | 126 (78.26%) | |
| CG | 11 (15.28%) | 8 (11.94%) | 26 (16.15%) | 0.763 |
| GG | 0 (0%) | 2 (2.98%) | 9 (5.59%) | 0.041 |

*mean PAP was only measured in 14 normal subjects.
**P-values are calculated using ANOVA (mean PAP) and $X^2$ (Genotype) analysis for comparison between IPAH patients and normal subjects.

The occurrence of the −254G SNP variant coincident with −361T and −218T SNP variants and the occurrence of the −254G SNP variant coincident with "wild-type"-361A and −218C SNP variants in subjects with IPAH, SPH, and control subjects are shown in Table 15. In both the IPAH and SPH subjects, the difference between the two groups (group A versus group B) was significant (p<0.05; $X^2$ analysis) suggesting that the presence of the −254G SNP variant in a "wild-type" −361A and −218C SNP variant background could be used as a predictive marker for IPAH. As also shown in Table 15, the occurrence of the −254G SNP variant in both control or subjects with SPH in group A (having the −361T and −218T SNP variants) are similar suggesting that the −254G SNP variant does not significantly coincide with the −361T and −218T SNP variants. This further confirms the observation above that the presence of −254G SNP variant in a "wild-type" −361A and −218C SNP variant background is more likely to predict IPAH than SPH.

TABLE 15

Genotype frequencies of the SNP (C-254G) with either -361T and
-218T variants or -361A and -218C variants in the TRPC6 gene
promoter in normal subjects and patients with SPH or IPAH

| Patient group | -254G with variant -361T and -218T (Group A) | -254G with "wild types" -361(A) and -218(C) (Group B) | P (A vs. B)* |
|---|---|---|---|
| IPAH | 8/66 | 27/95 | 0.0137 |
| SPH | 1/26 | 9/41 | 0.0427 |
| Normal | 2/29 | 9/43 | 0.1045 |

*P-values were calculated using $X^2$ analysis for comparison of the allele frequencies in IPAH patients with normal subjects and SPH patients.

As shown in Table 15, the P value for patients with IPAH indicates that the probability that the association of the −254G variant the associates with the "wild type" −361A and −218C SNP variants rather than the −361T and −218T variants, is significant. Furthermore, if the normal subjects and the SPH patient groups are combined together, the P value is still significant (P=0.0101; X2 analysis).

Idiopathic Pulmonary Arterial Hypertension

IPAH is a fatal and progressive disease with unknown etiology and which predominantly affects women. The elevated PVR and arterial pressure in IPAH patients result mainly from pulmonary vasoconstriction, vascular remodeling, and in situ thrombosis. A central aspect of pulmonary vascular remodeling is medial hypertrophy caused by sustained pulmonary vasoconstriction, excessive PASMC proliferation, and inhibited PASMC apoptosis, resulting in a narrowed vascular lumen and increased PVR. Although its etiology remains unclear, elevated levels of circulating mitogens, dysfunction or down-regulation of receptors and ion channels, upregulation of transporters, and heightened activity of elastases and glycoproteins have been implicated in IPAH.

Mutations of certain genes such as BMP receptor type II gene (BMPR2) and serotonin transporter gene (5-HTT) have recently been demonstrated to be the genetic basis for familial and idiopathic pulmonary arterial hypertension. BMPs are members of the TGF-β superfamily of growth-regulatory proteins. These results suggest that predisposition due to genetic variations in candidate genes may be involved in the development of the disease.

A rise in cytoplasmic $Ca^{2+}$ concentration ($[Ca^{2+}]_{cyt}$) can activate signal transduction proteins and transcription factors essential for cell proliferation. IPAH-PASMC show elevated resting $[Ca^{2+}]_{cyt}$ and enhanced $[Ca^{2+}]_{cyt}$ after mitogenic stimulation, whereas removal or chelation of extracellular $Ca^{2+}$ significantly inhibit serum and growth factor-induced PASMC growth. These observations indicate that enhanced $Ca^{2+}$ influx and elevated $[Ca^{2+}]_{cyt}$ are requisites for normal PASMC growth, whereas an excessive increase in $Ca^{2+}$ entry and the subsequent sustained increase in $[Ca^{2+}]cyt$ may be critical stimuli for IPAH-PASMC overgrowth. Increased $Ca^{2+}$ influx during PASMC proliferation was shown to be due largely to increased capacitative $Ca^{2+}$ entry (CCE). CCE is essential for maintaining a high level of $[Ca^{2+}]_{cyt}$ and for refilling intracellular $Ca^{2+}$ stores, such as the sarcoplasmic reticulum.

Transient receptor potential (TRP) channel genes may encode subunits that form receptor-(ROC) and store-(SOC) operated $Ca^{2+}$ channels in many cell types, including PASMC and pulmonary artery endothelial cells (PAEC), neurons, epithelial cells, cardiomyocytes, and sperm. $Ca^{2+}$ entry through ROC and SOC increases $[Ca^{2+}]_{cyt}$ allowing for phosphorylation of signal transduction proteins and transcription factors that are essential for the progression of the cell cycle. High levels of $[Ca^{2+}]_{cyt}$ and sufficient levels of $Ca^{2+}$ in the sarcoplasmic reticulum are required for vascular smooth muscle cell proliferation. Because they regulate sarcoplasmic reticulum and cytoplasmic $Ca^{2+}$, CCE and SOC may play significant roles in regulating cell proliferation.

The effect of BMP in embryonic development of the lung epithelium and branching of airways is well established. Serotonin (5-HT) is also known to be a co-activator of TGF-β. Kasho et al. Kidney Int. 54: 1083-1092 (1998). BMPs and TGF-β have recently been considered to influence airway inflammatory processes in adults due to their chemotactic activity on fibroblasts, myocytes, and inflammatory cells. Induction of such inflammatory pathways in, for example, intestinal epithelium and antigen-presenting cells, as well as production of interferons, cytokines, and TNF-α, is known to be mediated by the nuclear factor κB (NF-κB) family of transcription factors. Chamaillard et al. Cell. Microbiol. 5: 581-592. (2003).

NF-κB Activation Pathway

NF-κB was originally described as a DNA-binding activity that recognized a sequence 5'-GGGGACTTTCC-3' (SEQ ID NO: 1) in the immunoglobulin κ light chain gene enhancer in mature B cells. Sen and Baltimore, Cell 46: 705-716, (1986). For nearly two decades, the NF-κB activation pathway has been the focus of experimental investigation. This pathway is highly conserved among metazoans and plays key roles in immune responses, cell proliferation, inflammation, apoptosis, early embryonic development, and many other processes.

At least five members of heterodimeric mammalian NF-κB have been described: NF-κB1 (p50 and its precursor p105), NF-κB2 (p52 and its precursor p100), c-Rel, RelA (p65) and RelB, each of which has a 300-residue Rel homology domain. The C-terminal domains are responsible for dimerization with other Rel proteins, but sequence-specific interactions come primarily from loops in the N-terminal domain. (See, for example, Ghosh et al. (1998) Annu. Rev. Immunol. 16: 225-260; Siebenlist et al. (1994) Annu. Rev. Cell Biol. 10: 405-455; Verma et al. (1995) Genes Dev. 9: 2723-2735; Baldwin et al. (1996) Annu. Rev. Immunol. 14: 649-683; Karin et al. (2000) Annu. Rev. Immunol. 18: 621-663; Ghosh and Karin (2002) Cell 109: S81-S96; and Jacobs et al. (1998) Cell 95: 749-758.)

Members of the NF-κB family have been identified in various organisms, ranging from flies to mammals. Members of this transcription factor family have 35% to 61% identity to each other and all have the Rel homology domain.

In mammals, the most widely distributed κB-binding transcription factor is a heterodimer consisting of p50 and p65 (Rel-A) proteins. This transcription factor plays a central role in various responses, leading to host defense through rapid induction of gene expression. In particular, it controls the expression of various inflammatory cytokines, the major histocompatibility complex genes and adhesion molecules involved in tumor metastasis. Disregulation of NF-κB and its dependent genes has been associated with various pathological conditions including toxic/septic shock, graft versus host reaction, acute inflammatory conditions, acute phase response, viral replication, radiation damage, atherosclerosis, and cancer.

Unlike other transcription factors, the NF-κB proteins are held in the cytoplasm in an inactive state by an inhibitory subunit called IκB. Phosphorylation of IκB by an IκB kinase complex (IKK) and subsequent degradation of IκB enables NF-κB to translocate to the nucleus.

In the nucleus the NF-κB proteins bind to a specific transcriptional regulatory element (TRE), the κB site, having the consensus sequence motif 5'-GGGRNNYYCC-3'. Baldwin Annu. Rev. Immunol. 16: 649-681 (1996). Such κB site TREs have been identified in the promoter regions of many cellular and viral genes, such as neurotrophins. In most cases, transcriptional activation of the gene has been documented.

The activity of the NF-κB proteins can also be modulated by glucocorticoids via interaction of the glucocorticoid-glucocorticoid receptor complex with NF-κB proteins both in solution as well as at the TRE. Almawi and Melemedjian J. Mol. Endocrinol. 28: 69-78, (2002).

Translocation activation of NF-κB into the nucleus of the cell is induced by many agents, such as inflammatory cytokines (for example, tumor necrosis factor (TNF), lymphotoxin (LT), and interleukin (IL)-1), mitogens, bacterial products, protein synthesis inhibitors, oxidative stress ($H_2O_2$), ultraviolet light, and phorbol esters. Agents that can either downmodulate or upmodulate the activation of NF-κB may be used for therapeutic treatment for certain pathological conditions.

Pulmonary vasoconstriction and vascular smooth muscle hypertrophy both contribute to the elevated PVR in IPAH patients. Medial hypertrophy due to PASMC hyperplasia and hypertrophy in distal vessels accounts for some of the pulmonary vascular remodeling in IPAH patients. Identifying the factors involved in promoting PASMC proliferation could assist in the development of effective therapeutic approaches for patients with IPAH. Results suggest that overexpression of the canonical TRP channels (TRPC), such as TRPC3 and TRPC6 channels, may be another pathogenic mechanism involved in the increased PASMC proliferation, and may contribute to the development of pulmonary medial hypertrophy in IPAH patients. Development of drugs and compositions specifically targeting TRPC gene expression and TRPC channel function may enhance therapeutic efficiency for IPAH patients.

Example 2

Use of Small Interfering RNA (siRNA) for Regulating Expression of TRPC6 in vivo

A polynucleotide expression vector comprising SEQ ID NO: 5 is injected into the pulmonary vasculature of an experimental rat via a pulmonary arterial catheter. The polynucleotide expression vector also comprises an expression cassette that is induced to transcribe SEQ ID NO: 5 when exposed to animal tissue and animal expression factors in vivo. The lungs and pulmonary artery are harvested at pre-determined time points and the tissue is analyzed using Western blot analysis and immunohistological method to determine expression of mRNA encoding TRPC3 and TRPC6 and of TRPC3 protein and TRPC6 protein. The harvested pulmonary arteries can also be treated to isolate PASMC for cell culture analyses.

In further experiments, a group of the experimental rats are pre-treated with 10% oxygen for one week to experimentally induce hypoxia in the animal. The polynucleotide expression vector comprising SEQ ID NO: 5 is injected into the pulmonary vasculature as described above.

The Pulmonary Arterial Pressure (PAP) is measured by a catheter placed in the main pulmonary artery via the internal jugular vein. PAP is compared between rats treated (or injected) with the polynucleotide expression vector comprising SEQ ID NO: 5 and control rats injected with a scrambled siRNA vector (which serves as a nonsilencing control). After measurement of PAP, tissues are harvested as described above and levels of mRNA encoding TRPC6 and levels of TRPC6 protein are determined using methods well known in the art.

To measure the effect of SEQ ID NO: 2 on transcriptional and translational regulation of TRPC6, the above siRNA are repeated but using a polynucleotide expression vector comprising SEQ ID NO: 2.

Example 3

Northern Analysis

Analogous computer techniques applying BLAST analysis is used to search for identical or related molecules in nucleotide databases such as GenBank database. The basis of the search is the product score that is defined as: (percent sequence identity×percent maximum BLAST score) divided by 100. The product score takes into account both the degree of similarity between two sequences and the length of the sequence match. Similar or related molecules are identified by selecting those that show product scores between 8 and 40.

The results of northern analyses are reported as a percentage distribution of libraries in which the transcript encoding the mammalian protein occurred. Analysis involves the categorization of cDNA libraries by organ/tissue and disease. The organ/tissue categories include cardiovascular, dematologic, developmental, endocrine; gastrointestinal, hematopoietic/immune, musculoskeletal, nervous, reproductive, and urologic. The disease categories included cancer, cardiovascular, inflammation/trauma, cell proliferation, and neurological disorders.

Example 4

Extension of Nucleic Acid Molecules

At least one of the nucleic acid molecules used to assemble a TRPC6 polynucleotide is produced by extension of a cDNA clone using oligonucleotide primers. One primer is synthesized to initiate 5' extension of the known fragment, and the other, to initiate 3' extension. The initial primers are designed using OLIGO 4.06 primer analysis software (National Biosciences) to be about 22 to 30 nucleotides in length, to have a GC content of about 50%, and to anneal to the target sequence at temperatures of about 55° C. to about 68° C. Any fragment that would result in hairpin structures and primer-primer dimerizations is avoided. Selected human cDNA libraries are used to extend the molecule. If more than one extension is needed, additional or nested sets of primers are designed.

High fidelity amplification is obtained by performing PCR in 96-well plates using the DNA ENGINE thermal cycler (MJ Research). The reaction mix contains DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3 and 4 repeated 20 times; Step 6: 68° C., 5 min; Step 7: storage at 4° C. In the alternative, when using a sequence inserted into a plasmid vector, parameters for the primer pair, T7 and SK+ (Stratagene), are as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7 storage at 4° C.

The concentration of DNA in each well is determined by dispensing 100 μl PICOGREEN quantitation reagent (0.25% (v/v); Molecular Probes) dissolved in 1×TE and 0.5 μl of undiluted PCR product into each well of an opaque fluorimeter plate (Corning Costar, Acton Mass.) and allowing the DNA to bind to the reagent. The plate is scanned in a Fluoroskan II (Labsystems Oy, Helsinki, Finland) to measure the fluorescence of the sample and to quantify the concentration of DNA. A 5 μl to 10 μl aliquot of the reaction mixture is analyzed by electrophoresis on a 1% agarose mini-gel to determine which reactions are successful in producing longer sequence.

The extended sequences are desalted, concentrated, transferred to 384-well plates, digested with CviJI cholera virus endonuclease (Molecular Biology Research, Madison Wis.), and sonicated or sheared prior to religation into pUC18 vector (Amersham Pharmacia Biotech). For shotgun sequencing, the digested fragments are separated on about 0.6-0.8% agarose gels, fragments were excised as visualized under UV light, and agar removed/digested with AGARACE (Promega). Extended fragments are religated using T4 DNA ligase (New England Biolabs) into pUC 18 vector (Amersham Pharmacia Biotech), treated with Pfu DNA polymerase (Stratagene) to fill-in restriction site overhangs, and transformed into competent E. coli cells. Transformed cells are selected on antibiotic-containing media, and individual colonies were picked and cultured overnight at 37° C. in 384-well plates in LB/2× carbenicillin liquid media.

The cells are lysed, and DNA is amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA is quantified by PICOGREEN reagent (Molecular Probes) as described above. Samples with low DNA recoveries are reamplified using the conditions described above. Samples are diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE terminator cycle sequencing ready reaction kit (PE Biosystems).

In like manner, the nucleic acid molecule of SEQ ID NO:2 or SEQ ID NO: 5 is used to obtain regulatory sequences using the procedure above, oligonucleotides designed for outward extension, and a genomic DNA library.

Example 5

Labeling of Probes and Hybridization Analyses

Nucleic acids are isolated from a biological source and applied to a substrate for standard hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probes are made from mRNA templates. Five micrograms of mRNA is mixed with 1 µg random primer (Life Technologies), incubated at 70° C. for 10 minutes, and lyophilized. The lyophilized sample is resuspended in 50 µl of 1× first strand buffer (cDNA Synthesis systems; Life Technologies) containing a dNTP mix, [$\alpha$-$^{32}$P]dCTP, dithiothreitol, and MMLV reverse transcriptase (Stratagene), and incubated at 42° C. for 1-2 hours. After incubation, the probe is diluted with 42 µl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionucleotide, [$^{32}$P]dCTP.]

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probes. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using gene expression analysis software.

Example 6

Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (for example, PNAs). Oligonucleotides are designed using OLIGO 4.06 primer analysis software (National Biosciences). To inhibit transcription by preventing a transcription factor binding to a promoter, a complementary oligonucleotide is designed to bind to the most unique 5' sequence, most preferably between about 500 to 10 nucleotides before the initiation codon of the open reading frame. To inhibit translation, a complementary oligonucleotide is designed to prevent ribosomal binding to the mRNA encoding the mammalian protein.

Example 7

Production of SNP- and SNP-NF-κB-Specific Antibodies

The SNP or the SNP-NF-κB conjugate is purified using polyacrylamide gel electrophoresis and used to immunize mice or rabbits. Antibodies are produced using the protocols below. Rabbits are immunized with the SNP or the SNP-NF-κB complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

Example 8

Screening Molecules for Specific Binding with the Nucleic Acid Molecule or Protein Conjugate The nucleic acid molecule, or fragments thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Similarly, the SNP-NF-κB conjugate can be labeled with radionucleide or fluorescent probes. Libraries of candidate molecules or compounds previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

Example 9

Gel Shift Analysis

Electrophoretic mobility shift assays are performed using in vitro transcribed, translated NF-κB proteins. Proteins (1 µl each) are incubated for 20 minutes at room temperature with 100,000 cpm of Klenow-labeled probes in 10 mM Tris pH 8, 100 mM KCl, 6% glycerol, 0.05% NP-40, 1 mM dithiothreitol (DTT), 100 ng/µl poly dI:dC (Pharmacia, Piscataway N.J.) and then electrophoresed through a 5% polyacrylamide gel in 0.5×TBE (45 mM Tris-base, 45 mM boric acid, 1 mM ethylenediaminetetraacetic acid (EDTA) at room temperature. For competition binding, protein plus unlabeled oligonucleotides at five or fifty fold molar excess are preincubated for ten minutes on ice, then labeled probes are added and incubated for 20 minutes at room temperature. Electrophoresis is as above.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention. Specifically intended to be within the scope of the present invention, and incorporated herein by reference in its entirety, is the following publication: Yu et al., "Enhanced expression of transient receptor potential channels in idiopathic pulmonary arterial hypertension." PNAS. 101:13861-66 (2004).

What is claimed is:

1. A method of treating IPAH in a subject, the method comprising:
   a) determining if the subject has a C-254G TRPC6 SNP comprising a G in position −254; and
   b) administering to the subject a therapeutically effective amount of a compound that reduces a biological activity of TRPC6 if the subject has the SNP.

2. A method according to claim 1, wherein the subject is a human.

3. A method according to claim 1, wherein the compound that reduces a biological activity of TRPC6 is selected from the group consisting of an siRNA, an antisense nucleic acid, a ribozyme, an antibody, a polypeptide fragment, and a peptidomimetic.

4. A method according to claim 1, wherein compound that reduces a biological activity of TRPC6 is selected from the group consisting of a compound that reduces amount of mRNA encoding TRPC6 polypeptide, and a compound that reduces amount of TRPC6 polypeptide.

5. A method according to claim 4, wherein the TRPC6 inhibitor is a compound that reduces amount of mRNA encoding TRPC6.

6. A method according to claim 5, wherein the TRPC6 inhibitor is an siRNA to TRPC6 mRNA.

7. A method according to claim 6, wherein the siRNA is a double stranded siRNA comprising an RNA sequence corresponding to SEQ ID NO: 4 and the complement thereof.

8. A method according to claim 6, wherein the double stranded RNA comprises an RNA sequence corresponding to SEQ ID NO: 5 and the complement thereof.

9. A method according to claim 5, wherein the compound that reduces amount of mRNA encoding TRPC6 comprises an expression vector comprising SEQ ID NO: 5, wherein the expression vector comprises an expression cassette that may be induced to transcribe SEQ ID NO: 5.

10. A method according to claim 4, wherein the compound that reduces amount of TRPC6 polypeptide is a TRPC6 antibody or a fragment thereof.

11. A method according to claim 10, wherein the antibody is a monoclonal antibody.

* * * * *